United States Patent
Bisgaier et al.

(10) Patent No.: US 8,119,590 B2
(45) Date of Patent: Feb. 21, 2012

(54) PREVENTION AND TREATMENT OF RESTENOSIS BY LOCAL ADMINISTRATION OF DRUG

(75) Inventors: Charles L. Bisgaier, Ann Arbor, MI (US); Prediman Krishan Shah, Los Angeles, CA (US); Sanjay Kaul, Los Angeles, CA (US)

(73) Assignees: Cedars-Sinai Medical Center, Los Angeles, CA (US); Esperion Therapeutics, Inc, Ann Arbor, MI (US)

( * ) Notice: Subject to any disclaimer, the term of this patent is extended or adjusted under 35 U.S.C. 154(b) by 312 days.

(21) Appl. No.: 10/260,094

(22) Filed: Sep. 27, 2002

(65) Prior Publication Data
US 2003/0109442 A1    Jun. 12, 2003

Related U.S. Application Data

(60) Provisional application No. 60/326,379, filed on Sep. 28, 2001.

(51) Int. Cl.
| A61K 38/00 | (2006.01) |
| A61K 47/00 | (2006.01) |
| A61K 35/34 | (2006.01) |
| A61K 35/44 | (2006.01) |
| C07K 2/00 | (2006.01) |
| C07K 4/00 | (2006.01) |
| C07K 5/00 | (2006.01) |
| C07K 14/00 | (2006.01) |
| C07K 16/00 | (2006.01) |
| C07K 17/00 | (2006.01) |

(52) U.S. Cl. ............ 514/1.1; 514/1.2; 424/569; 530/300
(58) Field of Classification Search ...................... 514/12
See application file for complete search history.

(56) References Cited

U.S. PATENT DOCUMENTS

| 4,868,116 | A | 9/1989 | Morgan et al. |
| 4,970,144 | A | 11/1990 | Fareed et al. |
| 4,980,286 | A | 12/1990 | Morgan et al. |
| 5,643,757 | A * | 7/1997 | Malik et al. ............... 435/69.7 |
| 5,721,114 | A | 2/1998 | Abrahamsen et al. |
| 5,827,516 | A | 10/1998 | Urban et al. |
| 5,834,596 | A | 11/1998 | Ageland et al. |
| 5,861,276 | A | 1/1999 | Kwak et al. |
| 5,876,968 | A * | 3/1999 | Sirtori et al. ............... 435/69.7 |
| 5,972,890 | A | 10/1999 | Lees et al. |
| 5,990,081 | A | 11/1999 | Ageland et al. |
| 6,004,925 | A * | 12/1999 | Dasseux et al. ................ 514/2 |
| 6,037,323 | A | 3/2000 | Dasseux et al. |
| 6,046,166 | A | 4/2000 | Dasseux et al. |
| 6,080,422 | A | 6/2000 | Williams |
| 6,090,921 | A | 7/2000 | Winge et al. |
| 6,107,467 | A | 8/2000 | Ageland et al. |
| 6,258,596 | B1 | 7/2001 | Benoit et al. |
| 6,265,377 | B1 | 7/2001 | Dasseux et al. |
| 6,329,341 | B1 | 12/2001 | Dasseux et al. |
| 6,376,464 | B1 | 4/2002 | Dasseux et al. |
| 6,423,830 | B1 | 7/2002 | Winge et al. |
| 6,506,799 | B1 * | 1/2003 | Dasseux ....................... 514/715 |
| 6,506,879 | B1 | 1/2003 | Ageland et al. |
| 6,559,284 | B1 | 5/2003 | Ageland et al. |
| 6,617,134 | B1 | 9/2003 | Sirtori et al. |
| 6,635,623 | B1 | 10/2003 | Hoogeveen et al. |
| 6,727,102 | B1 | 4/2004 | Holvoet et al. |
| 6,773,719 | B2 * | 8/2004 | Rodrigueza et al. ........... 424/450 |
| 7,351,421 | B2 * | 4/2008 | Sung et al. ..................... 424/422 |
| 7,435,717 | B2 * | 10/2008 | Bisgaier et al. .................... 514/2 |
| 2002/0156007 | A1 * | 10/2002 | Graversen et al. .............. 514/12 |

(Continued)

FOREIGN PATENT DOCUMENTS

EP    0267703    6/1991

(Continued)

OTHER PUBLICATIONS

Sharifi B.G. et al., Adeno-associated virus-mediated apo A-1 milano genetherapy for atherosclerosis and restenosis, Journal of the American College of Cardiology, Elsevier, New York, NY, 37:2, Supplement A, Feb. 2001, 2 pages. (Cited in IDS of Aug. 31, 2010).*

(Continued)

*Primary Examiner* — Maury Audet
(74) *Attorney, Agent, or Firm* — Linda B. Truong; Davis Wright Tremaine

(57) ABSTRACT

Apolipoprotein A-I (ApoA-I), preferably a variant form such as Apolipoprotein A-I Milano (ApoA-IM), alone or more preferably in combination with a lipid carrier such as phospholipids or other drug, can be administered locally before or during bypass surgery on diseased coronary, peripheral, and cerebral arteries, surgery to implant grafts or transplanted organs, or angioplasty, or to stabilize unstable plaques. In an alternative embodiment, the apolipoprotein is not provided directly, but the gene encoding the apolipoprotein is provided. The gene is introduced into the blood vessel in a manner similar to that used for the protein, where the protein is then expressed. The technique can also be used for delivery of genes for treatment or prevention or restenosis or other cardiovascular diseases. In yet another embodiment, stents are coated with apolipoproteins alone, apolipoproteins formulated with lipids, genetically engineered cells expressing the apolipoproteins, naked DNA coding for an apolipoprotein, or other drugs such as anti-proliferatives for local delivery to an injury site. In a preferred embodiment, the system is used with combination therapy, with for local delivery of an agent such as an apolipoprotein in combination with systemic anti-hypertension therapy, anti-inflammatoy therapy, lipid regulation and/or anti-coagulation therapy. These treatments can begin prior to, concurrent with or following local delivery.

35 Claims, 9 Drawing Sheets

U.S. PATENT DOCUMENTS

Figure 1B:
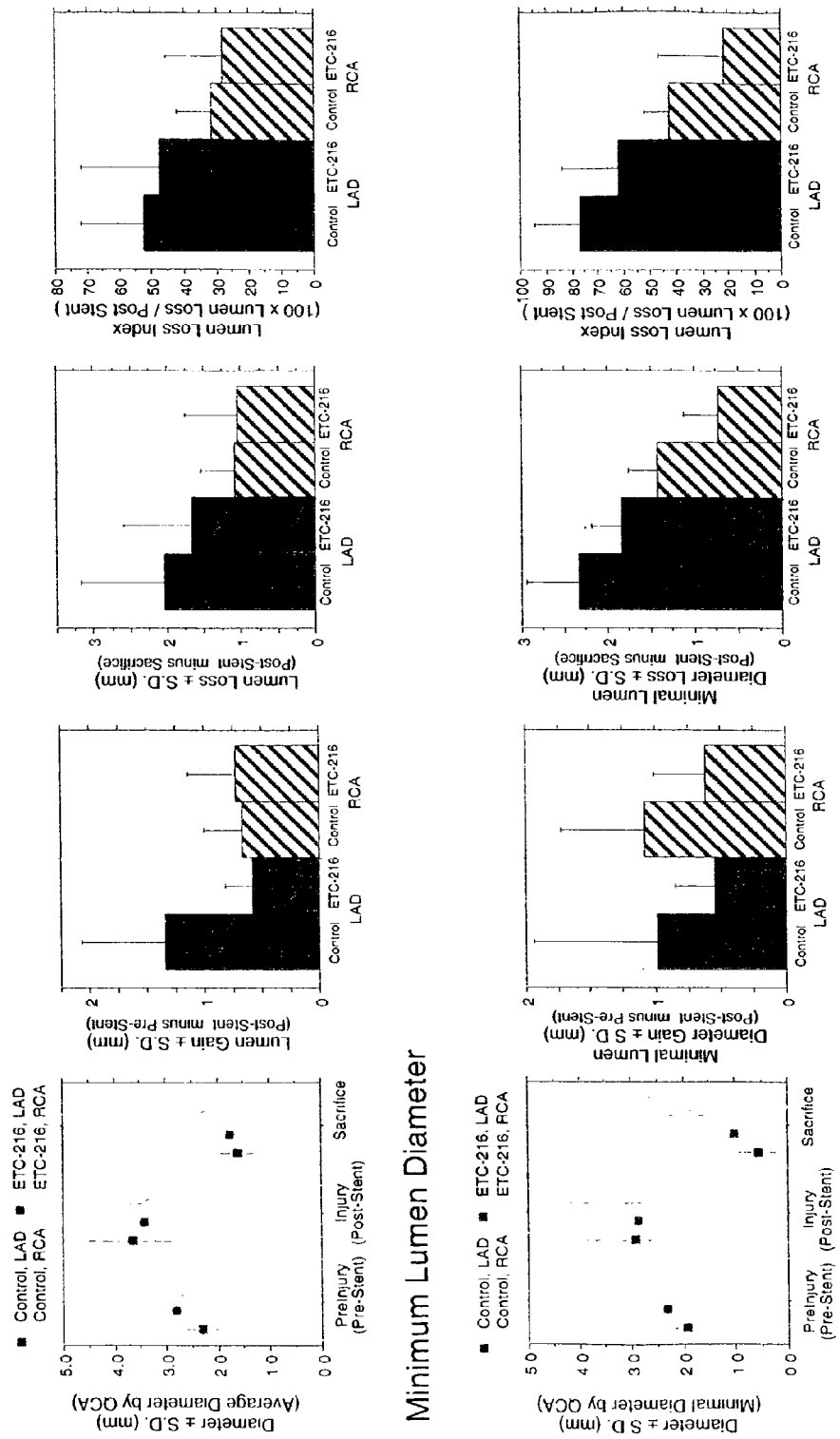
Figure 2A:
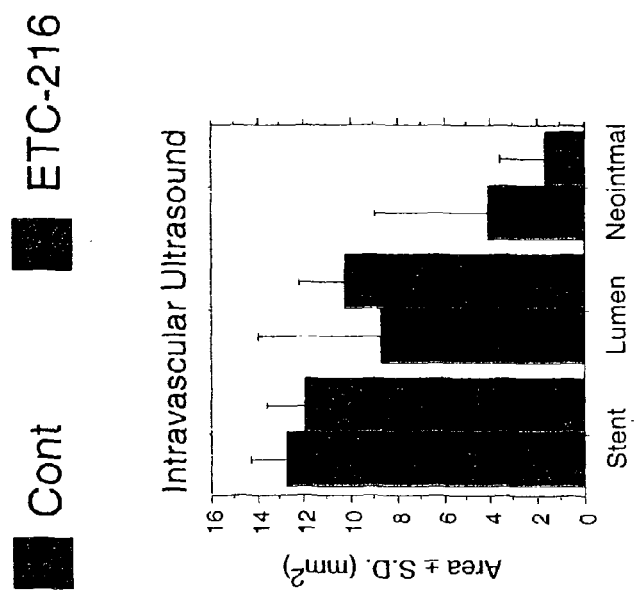
Figure 2B:
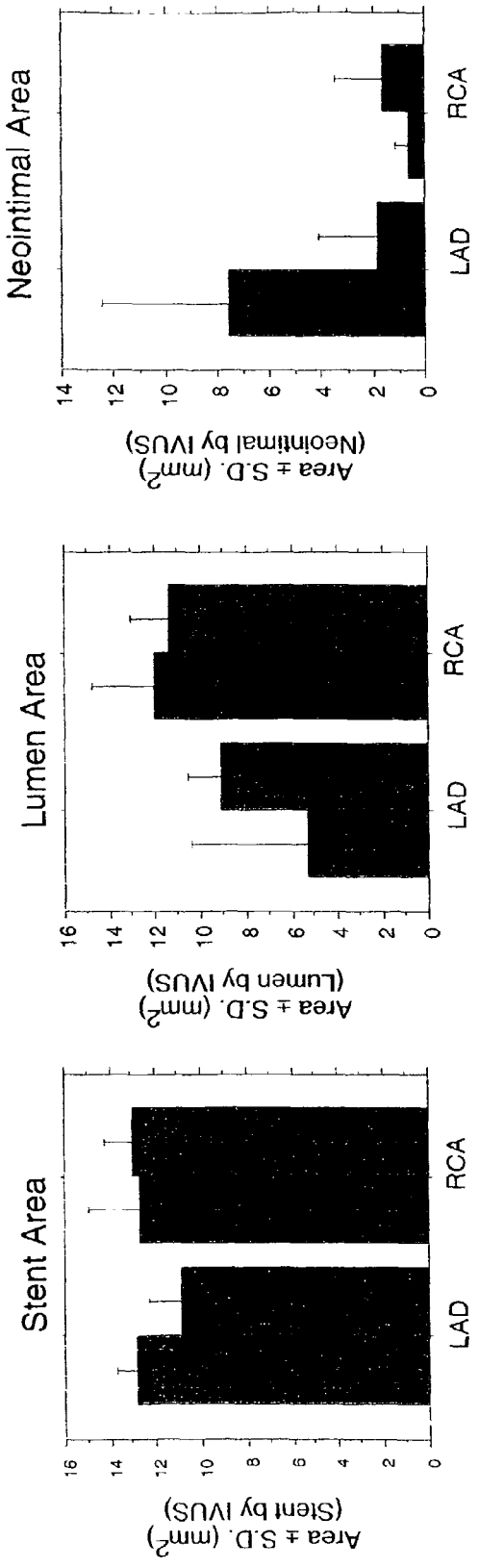
Figure 3A:
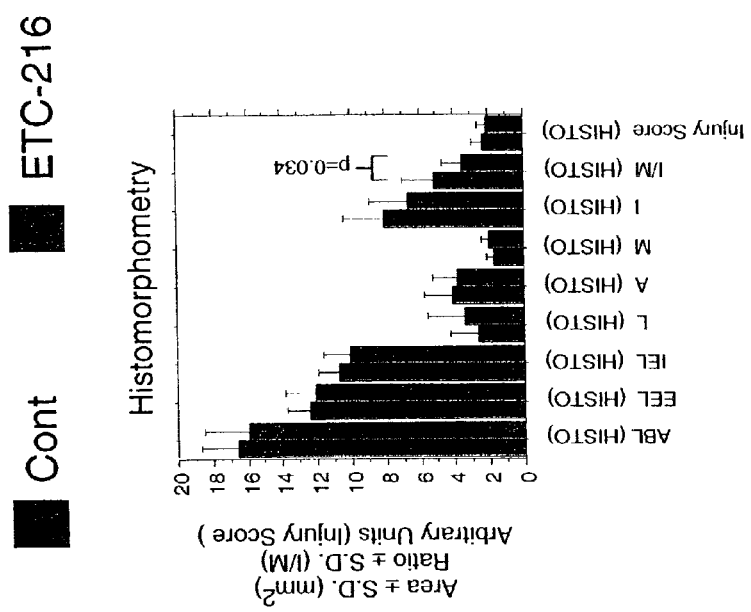
Figure 3B:
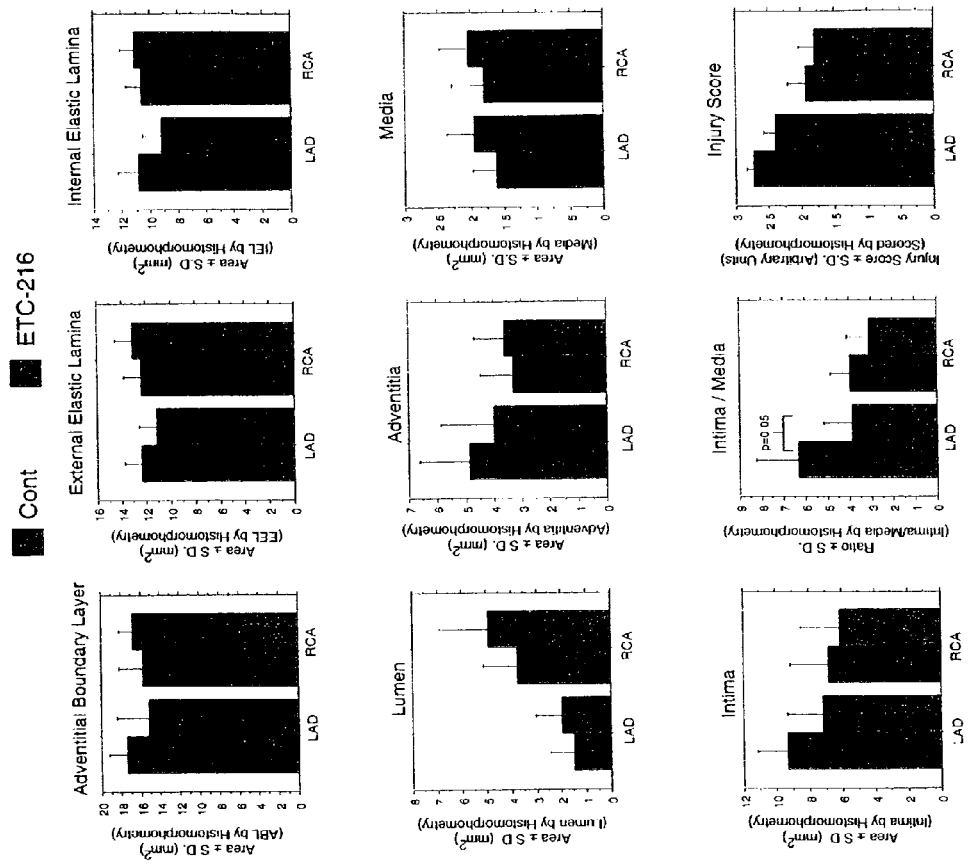

2003/0109442 A1 6/2003 Bisgaier et al.

FOREIGN PATENT DOCUMENTS

| EP | 0469017 | | 6/1994 |
|---|---|---|---|
| EP | 0494848 | | 3/1997 |
| EP | 0 911 344 | A1 | 4/1999 |
| EP | 1 186 299 | A1 | 3/2002 |
| EP | 1 394 177 | A1 | 3/2004 |
| JP | 08157492 | A * | 6/1996 |
| JP | 10025248 | A * | 1/1998 |
| WO | WO 89/07136 | | 8/1989 |
| WO | WO 90/02806 | | 3/1990 |
| WO | WO 90/12879 | * | 11/1990 |
| WO | WO 93/12143 | | 6/1993 |
| WO | WO 93-18067 | A1 | 9/1993 |
| WO | WO 94-00592 | | 1/1994 |
| WO | WO 95/23592 | | 9/1995 |
| WO | WO 96/37608 | | 11/1996 |
| WO | WO 97-43311 | | 11/1997 |
| WO | WO 99-08109 | | 2/1998 |
| WO | WO 98-13385 | | 4/1998 |
| WO | WO 98-42751 | | 10/1998 |
| WO | WO 98-56938 | | 12/1998 |
| WO | WO 99-18986 | A | 4/1999 |
| WO | WO 99-46598 | | 9/1999 |
| WO | WO 00-02920 | A1 | 1/2000 |
| WO | WO 01-32070 | A2 | 5/2001 |
| WO | WO 01-57274 | A2 | 8/2001 |
| WO | WO 01-64008 | A2 | 9/2001 |
| WO | WO 01-68119 | | 9/2001 |
| WO | WO 02-06314 | A2 | 1/2002 |
| WO | WO 02/30359 | | 4/2002 |
| WO | WO 02-42426 | | 5/2002 |
| WO | WO 02-48388 | A2 | 6/2002 |
| WO | WO 02-080954 | | 10/2002 |
| WO | WO 03-007689 | | 1/2003 |
| WO | 03/026492 | A3 | 4/2003 |
| WO | WO 03-026492 | | 4/2003 |
| WO | 2005/097206 | A3 | 10/2005 |
| WO | WO 2005-097206 | | 10/2005 |

OTHER PUBLICATIONS

Aviram, M., et al., "Paraoxonase Active Site Required for Protection Against LDL Oxidation Involves Its Free Sulfhydryl Group and Is Different From That Required for Its Arylesterase/Paraoxonase Activities: Selective Action of Human Paraoxonase Allozymes Q and R," (1998), Arterioscler. Thromb. Vasc. Biol., 18, pp. 1617-1624.

Aviram, M., et al., "Paraoxonase Inhibits High-Density Lipoprotein Oxidation and Preserves Its Functions: A Possible Peroxidative Role for Paraoxonase," (1998), J. Clin. Invest., 101, pp. 1581-1590.

Billecke, S., et al., "Human Serum Paraoxonase (PON1) Isozymes Q and R Hydrolyze Lactones and Cyclic Carbonate Esters," (2000), Drug Metab. Dispos., 28, pp. 1335-1342.

Bielicki, J.K., et al., "Evidence that Apolipoprotein A-1 $_{Milano}$ Has Reduced Capacity, Compared with Wild-Type Apolipoprotein A-I, to Recruit Membrane Cholesterol," (1997), Arterioscler. Thromb. Vasc. Biol., 17(9), pp. 1637-1643.

Calabresi, L., et al., "Increased Postprandial Lipemia in Apo A-IMilano Carriers," (1993), Arterioscler. and Thromb., 13(4), pp. 521-528.

Chiesa, G., et al., "Elevated Triglycerides and Low HDL Cholesterol in Transgenic Mice Expressing Human Apolipoprotein A-I$_{Milano}$," (1998), Atherscl, 136, pp. 139-146.

Dragonov, D.I., et al., "Rabbit Serum Paraoxonase 3 (PON3) Is a High Density Lipoprotein-Associated Lactonase and Protects Low Density Lipoprotein Against Oxidation," (2000), J. Biol. Chem., 275(43), pp. 33435-33442.

Franceschini, G., et al., "Apolipoprotein AI$_{Milano}$: Disulfide-Linked Dimers Increase High Density Lipoprotein Stability and Hinder Particle Interconversion in Carrier Plasma," (1990), J. Biol. Chem., 265(21), pp. 12224-12231.

Franceschini, G., et al., "Apolipoprotein AI$_{Milano}$: Accelerated Binding and Dissociation from Lipids of a Human Apolipoprotein Variant," (1985), J. Biol. Chem., 260(30), pp. 16321-16325.

Franceschini, G., et al., "Increased Cholesterol Efflux Potential of Sera From ApoA-I$_{Milano}$ Carriers and Transgenic Mice," (1999), Arterioscler. Thromb. Vasc. Biol., 19,pp. 1257-1262.

Franceschini, G., et al., "Relationship of the Phenotypic Expression of the A-I$_{Milano}$ Apoprotein with Plasma Lipid and Lipoprotein Patterns," (1985), Atherscl., 58, pp. 159-174.

Franceschini, et al. "Apolipoprotein A-I$_{Milano}$ Correlation between High Density Lipoprotein Subclass Distribution and Triglyceridemia," (1987) Arteriosclerosis 7:426-435.

Franceschini, G., et al., Altered Lipid Binding Properties in a Human Apolipoprotein Variant, (1988), Recent Aspects of Diagnosis and Treatment of Lipoprotein Disorders, pp. 73-80.

Gualandri, N., et al., "AI$_{Milano}$ Apoprotein Identification of the Complete Kindred and Evidence of a Dominant Genetic Transmission," (1985), Am. J. Hum. Genet., 37, pp. 1083-1097.

James, R.W., et al., "Modulated Serum Activities and Concentrations of Paraoxonase in High Density Lipoprotein Deficiency States,"(1998), Atherscl., 139, pp. 77-82.

Kaul, et al. "Intramural Delivery of Recombinant Apolipoprotein A-I$_{Milano}$ /Phospholipid Complex (ETC-216) Inhibits In-Stent Stenosis in Porcine Coronary Arteries," Circulation 107:2551-2554 (2003).

Li, D., et al., "Inhibition of Arterial Thrombus Formation by ApoA I Milano," (1999), Arterioscler. Thromb. Vasc. Biol., 19, pp. 378-383.

Nilsson et al., "Lipoprotein-Like Phospholipid Particles Inhibit the Smooth Muscle Cell Cytotoxicity of Lysophosphatidycholine and Platelet-Activating Factor," (1998), Arterioscler. Thromb. Vasc. Biol., 18, pp. 13-19.

Roma, et al., In Vivo Metabolism of a Mutant Form of Apolipoprotein A-I, APO A-I$_{Milano}$, Associated with Familial Hypoalphalipoproteinemia.

Rosseneu and Labeur, "Physiological Significance of Apolipoprotein Mutants," (1995), The FASEB Journal, 9, pp. 768-776.

Shah, P.K., et al., "Effects of Recombinant Apolipoprotein A-I$_{Milano}$ on Aortic Atherosclerosis in Apolipoprotein E-Deficient Mice," (1998), Circulation, 97, pp. 780-785.

Shah, et al.., "High-Dose Recombinant Apolipoprotein A-I$_{Milano}$ Mobilizes Tissue Cholesterol and Rapidly Reduces Plaque Lipid and Macrophage Content in Apolipoprotein E-Deficient Mice. Potential Implications for Acute Plaque Stabilization," (2001) Circulation 103:3047-3050.

Sirtori, C.R., et al., "Familial Disorders of Plasma Apolipoproteins," (1985), Klin Wochenschrift, 63, pp. 481-489.

Sirtori, C.R., et al., "Recombinant Apolipoproteins for the Treatment of Vascular Diseases," (1999), Atherscl., 142, pp. 29-40.

Sirtori, C.R., et al., "Apolipoprotein AI$_{Milano}$ (The First Molecular Variant of Human Apolipoprotein)," (1982), La Ricera Clin. Lab., 12, pp. 83-86.

Soma, M.R., et al., "Recombinant Apolipoprotein A-I$_{Milano}$ Dimer Inhibits Carotid Intimal Thickening Induced by Perivascular Manipulation in Rabbits," (1995), Circulation Res., 76,pp. 405-411.

Syvanne, M., et al., "Cholesterol Efflux from Fu5AH Hepatoma Cells Induced by Plasma of Subjects With or Without Coronary Artery Disease and Non-insulin-Dependent Diabetes: Importance of LpA-I:A-II Particles and Phospholipid Transfer Protein," (1996), Atherscl., 127, pp. 245-253.

Westman et al., "Sterol 27-Hydroxylase- and ApoAI/Phospholipid-Mediated Efflux of Cholesterol From Cholesterol-Laden Macrophages: Evidence for an Inverse Relation Between the Two Mechanisms," (1998), Arterioscler. Thromb. Vasc. Biol. 18, pp. 554-561.

Acsadi, "Human dystrophin expression in mdx mice after intramuscular injection of DNA constructs," Nature 352: 815-818 (1991).

Ameli, et al., "Recombinant apolipoprotein A-I Milano reduces intimal thickening after balloon injury in hypercholesterolemic rabbits," Circulation 90(4):1935-1941 (1994).

Badimon, et al., "High density lipoprotein plasma fractions Inhibit aortic fatty streaks in cholesterol-fed rabbits," Lab Invest 60(3):455-61 (1989).

Badimon, et al., "Regression of atherosclerotic lesions by high density lipoprotein plasma fraction in the cholesterol-fed rabbit" J Clin Invest 85(4):1234-41 (1990).

Banerji, et al., "A lymphocyte-specific cellular enhancer is located downstream of the joining region in immunoglobulin heavy chain genes," Cell 33(3): 729-740 (1983).

Berkner, et al., "Abundant expression of polyomavirus middle T antigen and dihydrofolate reductase in an adenovirus recombinant," J. Virol 61(4): 1213-1220 (1987).

Bielicki, et al., "Apolipoprotein A-I$_{Milano}$ and Apolipoproteln A-I$_{Paris}$ Exhibit an Antioxidant Activity Distinct from That of Wild-Type Apolipoprotein A-I," Biochemistry 41: 2089-2096 (2002).

Bout, et al., "Lung gene therapy: in vivo adenovirus-mediated gene transfer to rhesus monkey airway epithelium," Human Gene Therapy 5(1): 3-10 (1994).

Brehm, et al., "Prevention of human smooth muscle cell proliferation without induction of apoptosis by the topoisomerase I inhibitor topotecan," Biochemical Pharmacology 61(1):119-127 (2001).

Brewer, et al., "The amino acid sequence of human APOA-I, an apolipoprotein isolated from high density lipoproteins," Biochem Biophys Res Commun 80(3):623-30 (1978).

Brown, et al., "Penetration of host cell membranes by adenovirus 2," J. Virol. 12(2): 386-396 (1973).

Caillaud, et al., "Adenoviral vector as a gene delivery system Into cultured rat neuronal and glial cells," Eur. J. Neuroscience 5(10): 1287-1291 (1993).

Chardonnet, et al., "Early events in the interaction of adenoviruses with HeLa cells. I. Penetration of type 5 and intracellular release of the DNA genome," Virology 40(3): 462-477 (1970).

Chen, et al., "Nitric oxide synthase gene therapy for cardiovascular disease," Jpn. J. Pharmacol. 89(4):327-336 (2002).

Davidson, et al., "Overproduction of polyomavirus middle T antigen in mammalian cells through the use of an adenovirus vector," J. Virol. 61(4):1226-1239 (1987).

Eriksson, et al., "Stimulation of fecal steroid excretion after infusion of recombinant proapolipoprotein A-I. Potential reverse cholesterol transport in humans," Circulation 100: 594-598 (1999).

Fiers, et al., "Complete nucleotide sequence of SV40 DNA," Nature 273(5658): 113-120 (1978).

Fischman, et al., "A Randomized Comparison of Coronary-Stent Placement and Balloon Angioplasty in the Treatment of Coronary Artery Disease," N. E. J. Med. 331(8):496-501 (1994).

Franceschini, et al., "A-IMilano apoprotein. Decreased high density lipoprotein cholesterol levels with significant lipoprotein modifications and without clinical atherosclerosis in an Italian family," J. Clin. Invest. 66: 892-900 (1980).

Francis, et al. "Gene therapy in cardiovascular disease. Current status," Am. J. Pharmacogenomics 1(1):55.66 (2001).

Gòmez-Foix, et al., "Adenovirus-mediated transfer of the muscle glycogen phosphorylase gene into hepatocytes confers altered regulation of glycogen metabolism," J. Biol. Chem. 267(35): 25129-25134 (1992).

Greenway, et al., "Human cytomegalovirus DNA: BamH1, EcoR1 and Pst1 restriction endonuclease cleavage maps," Gene 18: 355-360 (1982).

Guzman, et al., "Efficient gene transfer into myocardium by direct injection of adenovirus vectors," Circ. Res. 73(6): 1202-1207 (1993).

Haj-Ahmad, et al., "Development of a helper-independent human adenovirus vector and its use in the transfer of the herpes simplex virus thymidine kinase gene," J. Virol. 57(1): 267-274 (1986).

Inoue, et al., "Expression of Polymorphonuclear Leukocyte Adhesion Molecules and Its Clinical Significance in Patients Treated With Percutaneous Transluminal Coronary Angioplasty," JACC 28(5):1127-1133 (1996).

Kipshidze, et al., "Intramural coronary delivery of advanced antisense oligonucleotides reduces neointimal formation in the porcine stent restenosis model," J. Am. Coll. Cardiol. 39(10): 1686-1691 (2002).

Kirshenbaum, et al., "Highly efficient gene transfer into adult ventricular myocytes by recombinant adenovirus," J. Clin. Invest. 92(1): 381-387 (1993).

La Salle, et al., "An adenovirus vector for gene transfer into neurons and glia in the brain," Science 259(5097): 988-990 (1993).

Laimins, et al., "Osmotic control of kdp operon expression In *Escherichia coli*," Proc. Nat. Acad. Sci.USA 78(1): 464-468 (1981).

Lusky, et al., "Bovine papilloma virus contains an activator of gene expression at the distal end of the early transcription unit," Mol. Cell Biol. 3(6): 1108-1122 (1983).

Massie, et al., "Construction of a helper-free recombinant adenovirus that expresses polyomavirus large T antigen," Mol. Cell. Biol. 6(8): 2872-2883 (1986).

Matsuda, et al., "Photoinduced prevention of tissue adhesion," ASAIO Trans., 38:154-157 (1992).

Mickelson, et al., "Leukocyte Activation With Platelet Adhesion After Coronary Angioplasty: A Mechanism for Recurrent Disease?" JACC 28(2):345-353 (1996).

Miyazaki, et al., "Intravenous injection of rabbit apolipoprotein A-I inhibits the progression of atherosclerosis in cholesterol-fed rabbits," Arterioscler. Thromb. Vasc. Biol. 15: 1882-1888 (1995).

Morsy, et al., "Efficient adenoviral-mediated ornithine transcarbamylase expression in deficient mouse and human hepatocytes," J. Clin. Invest. 92(3): 1580-1586 (1993).

Moullier, et al., "Correction of lysosomal storage in the liver and spleen of MPS VII mice by implantation of genetically modified skin fibroblasts," Nature Genetics 4(2): 154-159 (1993).

Mulligan, "The basic science of gene therapy," Science 260(5110): 926-932 (1993).

Nanjee, et al, "Acute effects of intravenous infusion of ApoA1/phosphatldylcholine discs on plasma lipoproteins in humans," Arterioscler. Thromb. Vasc. Biol. 19: 979-989(1999).

Osborne, et al., "Transcription control region within the protein-coding portion of adenovirus E1A genes," Mol. Cell Bio. 4(7): 1293-1305 (1984).

Pavlides, et al., "Intramural drug delivery by direct injection within the arterial wall: First clinical experience with a novel intracoronary delivery-infiltrator system," Cathet. Cardiovasc. Diagn. 41(3): 287-292 (1997).

Pepine, et al., "A Controlled Trial of Coricocosterolds to Prevent Restenosis After Coronary Angioplasty," Circulation 81(6)1753-1761 (1990).

Pietersma, et al., "Late Lumen Loss After Coronary Angioplasty Is Associated With the Activation Status of Circulating Phagocytes Before Treatment," Circulation 91(5):1320-1325 (1995).

Ragot, et al., "Replication-defective recombinant adenovirus expressing the Epstein-Barr virus (EBV) envelope glycoprotein gp340/220 induces protective immunity against EBV-induced lymphomas in the cottontop tamarin," J. Gen. Virol. 74(3): 501-507 (1993).

Ram, et al., "In situ retroviral-mediated gene transfer for the treatment of brain tumors in rats," Cancer Res. 53(1): 83-88, (1993).

Rich, et al, "Development and analysis of recombinant adenoviruses for gene therapy of cystic fibrosis," Human Gene Therapy 4(4): 461-476 (1993).

Roessler, et al., "Adenoviral-mediated gene transfer to rabbit synovium in vivo," J. Clin. Invest. 92(2): 1085-1092 (1993).

Segrest, et al., "A molecular theory of lipid-protein interactions in the plasma lipoproteins," FEBS Lett 38(3):247-58 (1974).

Serruys, et al., "A Comparison of Balloon-Expandable-Stent Implantation with Balloon Angioplasty in Patients with Coronary Artery Disease," N. E. J. Med. 331(8):489-495 (1994).

Seth, et al., "Evidence that the penton base of adenovirus Is involved in potentiation of toxicity of Pseudomonas exotoxin conjugated to epidermal growth factor," Mol. Cell. Biol. 4(8): 1528-1533 (1984).

Seth, et al., "Role of a low-pH environment in adenovirus enhancement of the toxicity of a Pseudomonas exotoxin-epidermal growth factor conjugate," J. Virol. 51(3): 650-655 (1984).

Svensson, "Role of vesicles during adenovirus 2 internalization into HeLa cells," J. Virol. 55(2): 442-449 (1985).

Teiger, et al., "Local gene delivery within the media of rabbit iliac arteries by using the infiltrator intramural delivery device," J. Cardiovasc. Pharmacol. 33(5): 726-732 (1999).

Turunen, et al., "Peptide-retargeted adenovirus encoding a tissue inhibitor of metalloproteinase-1 decreases restenosis after intravascular gene transfer," Mol. Ther. 6(3): 306 (2002).

Varga, et al., "Infectious entry pathway of adenovirus type 2," J. Virol. 65(11): 6061-6070 (1991).

Verma, "Retroviral vectors for gene transfer," in Microbiology,— 1985 (Leive, ed.) American Society for Microbiology: Washington D.C., pp. 229-232 (1985).

Weisgraber, et al., "A-Imilano apoprotein. Isolation and characterization of a cysteine-containing variant of the A-I apoprotein from human high density lipoproteins," J. Clin. Invest. 66: 901-907 (1980).

Wickham, et al., "Integrins $\square_v\square_3$ and $\square_v\square_5$ promote adenovirus Internalization but not virus attachment," Cell 73(2): 309-319 (1993).

Wolff, et al., "Conditions affecting direct gene transfer into rodent muscle in vivo," BioTechniques 11(4): 474-485 (1991).

Wolff, et al., "Direct gene transfer into mouse muscle in vivo," Science 247(4949): 1465-1468 (1990).

Zabner, et al., "Adenovirus-mediated gene transfer transiently corrects the chloride transport defect in nasal epithelia of patients with cystic fibrosis," Cell 75(2): 207-216 (1993).

Zabner, et al., "Safety and efficacy of repetitive adenovirus-mediated transfer of CFTR cDNA to airway epithelia of primates and cotton rats," Nat. Genet. 6(1): 75-83 (1994).

Zhang, et al., "Generation and identification of recombinant adenovirus by liposome-mediated transfection and PCR analysis" BioTechniques 15(5): 868-872 (1993).

International Search Report dated Jul. 3, 2003 for PCT/US02/31068 filed Sep. 27, 2002, 2 pages.

International Preliminary Examination Report dated Jun. 28, 2004 for PCT/US02/31068 filed Sep. 27, 2002, 3 pages.

Search Report for dated Aug. 23, 2005 European patent application No. 02799686.7 filed Sep. 27, 2002, 3 pages.

Examination Report dated Jan. 8, 2010 European patent application No. 02799686.7 filed Sep. 27, 2002, 4 pages.

Restriction Requirement mailed Mar. 25, 2009 for U.S. Appl. No. 10/599,692, filed Oct. 5, 2006, 8 pages.

Non-final Office Action mailed Aug. 6, 2009 for U.S. Appl. No. 10/599,692, filed Oct. 5, 2006, 7 pages.

Final Office Action mailed Mar. 24, 2010 for U.S. Appl. No. 10/599,692, filed Oct. 5, 2006, 10 pages.

International PCT Search Report and Written Opinion dated Dec. 29, 2005 for PCT/US05/11466 filed Apr. 5, 2005, 7 pages.

International Preliminary Report on Patentability dated Oct. 11, 2006 for PCT/US05/11466 filed Apr. 5, 2005, 4 pages.

European Search Report dated Apr. 4, 2007 for European patent application No. 05763769.6 filed Apr. 4, 2005, 3 pages.

Examination Report dated Aug. 21, 2007 for European patent application No. 05763769.6 filed Apr. 4, 2005, 4 pages.

Examination Report dated Jun. 25, 2008 for European patent application No. 05763769.6 filed Apr. 4, 2005, 7 pages.

Examination Report dated Jul. 23, 2009 for Japanese patent application No. 2007-507425 filed Apr. 4, 2005, 5 pages.

Fan et al., Efficient coexpression and secretion of anti-atherogenic human apolipoprotein AI and lecithin-cholesterol acyltransferase by cultured muscle cells using adeno-associated virus plasmid vectors, Gene Therapy (1998) 5, pp. 1434-1440.

Nissen, S.E. et al., Effect of Recombinant ApoA-1 Milano on Coronary Atherosclerosis in Patients With Acute Coronary Syndromes, JAMA, vol. 290, No. 17, pp. 2292-2300 (Nov. 2003).

Oka et al. Cardiovascular Summary, ASGT News, Annual Meeting Highlights, Fall, 2003, Washington, D.C.

Pastore et al., Helper-dependent adenoviral vector-mediated long term expression or human apolipoprotci, A-1 reduces atherosclerosis in apo E-deficient mice. Gene. Mar. 2004, vol. 327, No. 2, pp. 153-160.

Patel et al., rAAV-Mediated Apolipoprotein A-1 Milano Gene Therapy for Atherosclerosis, Molecular Therapy, vol. 7, No. 5, May 2003 Abstract Only.

Shah et al., Exploiting the vascular protective effects of high density lipoprotein and its apolipoproteins: an ideas whose time for testing is coming, Part II., Circulation, vol. 104, 2001, pp. 2498-2502.

Shah et al., Transplanation of bone marrow cells transduced with adeno-associated virus vectors encoding the apo A-1 milano gene inhibits atherosclerosis in apo E-null mice., Circulation, vol. 110, No. 17S, Oct. 26, 2004, pp. 330-331.

Shah et al., A Single intramuscular injection of recombinant adeno-associated virus vectors encoding the apo A-1 milano gene inhibits atherosclerosis in apo E-null mice., Circulation, vol. 110, No. 17S, Oct. 26, 2004, p. 330.

Sharifi B.G. et al., Andeno-associated virus-mediated apo A-1 milano genetherapy for atherosclerosis and restenosis, Journal of the American College of Cardiology, Elsevier, New York, NY, 37:2, Supplement A, Feb. 2001, 2 pages.

Sharifi B.G. et al., AAV serotype-dependent apolipoprotein A-I milano gene expression, Atherosclerosis 181, 2005, Elsevier, pp. 261-269.

Wang, Xiaosong et al., Comparative genetics of atherosclerosis and restenosis: exploration with mouse models, Arterioscler Thromb Vasc Biol., 22: Jun. 2002, (http://www.atvbaha.org), pp. 884-886.

Gandjini, H. et al., Resistance to LDL oxidative modifications of an N-terminal apolipoprotein B epitope. Atherosclerosis 1991 89:83-93.

Chauhan, et al., Evidence for lipid-dependent structural changes in specific domains of apolipoprotein B100. Biochemistry 1998 37:3735-3742.

Zhou, Xinghua et al., LDL immunization induces T-cell-dependent antibody formation and protection against atherosclerosis. Atherosclerosis, Thrombosis and Vascular Biology 2001 vol. 21, No. 1, pp. 108-114.

George, J et al., Hyperimmunization of ApoE-deficient mice with homologous malondialdehyde low-density lipoprotein suppresses early atherogenesis. Atherosclerosis 1998, vol. 138, pp. 147-152.

Palinski, W. et al., Immunization of low density lipoprotein (LDL) receptor-deficient rabbits with homologous malondialdehyde-modified LDL reduces atherogenesis. Proceedings of the National Academy of Sciences 1995, vol. 92 pp. 821-825.

Palinski, W. et al., Antisera and monoclonal antibodies specific for epitopes generated during oxidative modification of low density lipoprotein. Atherosclerosis 1990 vol. 10, pp. 324-335.

Rosenfeld, M. E. et al. Distribution of oxidation specific lipid-protein adducts and apolipoprotein B in atherosclerotic lesions of varying severityfrom WHHL rabbits. Atherosclerosis 1990 vol. 10 pp. 336-349.

Lefvert, A K. Heterogeneity of autoantibodies against cardiolipin and oxidatively modified LDLs revealed by human monoclonal antibodies. Journal of Internal Medicine Mar. 1, 2000 vol. 247 pp. 385-390.

Dunning, A M. et al., Association between epitopes detected by monoclonal antibody BIP-45 and the xbal polymorphisms of apolipoprotein B. Clinical Genetics,Jan. 1, 1998, vol. 33 pp. 181-188.

Young, Stephen G et al., Definition of a nonlinear conformational epitope for the apolipoprotein B-100 specific monoclonal antibody MB47 Journal of Lipid Research Jan. 1, 1994 vol. 35 pp. 399-407.

Fredrikson Gunilla Nordin et al., Inhibition of atherosclerosis in apo E null mice by imunization with native and MDA-modified modified apoB peptide sequences. Journal of the American College of Cardiology 2003 vol. 39 p. 240A.

Fredrikson Gunilla Nordin et al., Atheroprotective immunization with MDA-modified apoB-100 peptide sequences is associated with activation of TH2 specific antibody expression Autoimmunity 2005 vol. 38 pp. 171-179.

Shih, Ing Lung et al., Focal accumulation of an apolipoprotein B-based synthetic oligopeptide in the healing rabbit arterial wall. Proceedings of the National Academy of Sciences 1990 vol. 87 pp. 1436-1440.

Chen S-H et al., Apolipoprotein B-48 is the product of a messenger RNA with an organ-specific in-frame stop codon Science Oct. 16, 1987 vol. 238 pp. 363-366.

Valentinova, N. V. et al., Immunoreactivity of Apolipoprotein B-100 in oxidatively modified low density lipoprotein. Biological Chemistry 1994 vol. 375 pp. 651-658.

Tailleux, A et al., Immunological properties of ApoB-containing lipoprotein particles in human ahterosclerotic arteries Journal of Lipid Research Jan. 1, 1993 vol. 34 pp. 719-728.

McCormick et al., Mutagenesis of the human apolipoprotein B gene in a yeast artificial chromosome reveals the site of attachment for apolipoprotein(a). Proc Natl Acad Sci USA 92:10147-10151, 1995.

Pease et al., Use of bacterial expression cloning to localize the epitopes for a series of monoclonal antibodies against apolipoprotein B100. J Biol Chem 265(1): 553-568, 1990.

Milne et al., The use of monoclonal antibodies to localize the low density lipoprotein receptor-binding domain of apolipoprotein B. J Biol Chem 264(33): 19754-19760, 1989.

Wang, et al., Well-defined regions of apolipoprotein B-100 undergo conformational change during its intravascular metabolism. Arterioscler Thromb Vasc Biol 20: 1301-1308, 2000.

Schiopu et al., Recombinant human antibodies against aldehyde-modified apolipoprotein B-100 peptide sequences inhibit atherosclerosis. Circulation 110: 2047-2052, 2004.

Latif, et al., Liposomes in immunology. J Biosci 6(4): 491-502, 1984.

Chou, H., et al., Prediction of the Secondary Structure of Proteins from their Amino Acid Sequence, Advances in Enzymology and Related Areas of Molecular Biology, 1978; vol. 47, 104 pages.

Margalit, H., et al., Prediction of Immunodominant Helper T Cell Antigenic Sites from the Primary Sequence, The Journal of Immunology, 1987, vol. 138, pp. 2213-2229.

Jameson, B., et al., The Antigenic Index: a Novel Algorithm for Predicting Antigenic Determinants, 1988, vol. 4, pp. 181-186.

Reyes, V., et al., Prediction of $\alpha$ Helices and T Cell-Presented Sequences in Proteins with Algorithms Based on Strip-of-Helix Hydrophobicity Index, 1991, vol. 202, pp. 225-238.

Maksyutov, A., et al., ADEPT: A Computer Program for Prediction of Protein Antigenic Determinants, 1993, vol. 9, pp. 291-197.

Pellequer, J., et al., PREDITOP: A Program for Antigenicity Prediction, 1993, vol. 3, 1 page, Abstract only.

Lu, S., et al., Common Principles in Protein Folding and Antigen Presentation, 1991, vol. 9, pp. 238-242.

Raddrizzani, L., et al., Epitope Scanning Using Virtual Matrix-Based Algorithms, 2000, vol. 1, pp. 179-189.

OA for U.S. Appl. No. 10/599,692, dated Mar. 24, 2010, 7 pages.

OA for U.S. Appl. No. 10/599,692, dated Aug. 6, 2009, 6 pages.

Herzyk et al., Biochim Biophys Acta 922: 145-154, 1987.

Chehin, et al., Early stages of LDL oxidation: apolipoprotein B structural changes monitored by infrared spectroscopy. J Lipid Res 42: 778-782, 2001.

European Search Report dated Apr. 4, 2007 for European Patent Application No. 05763769.6.

* cited by examiner

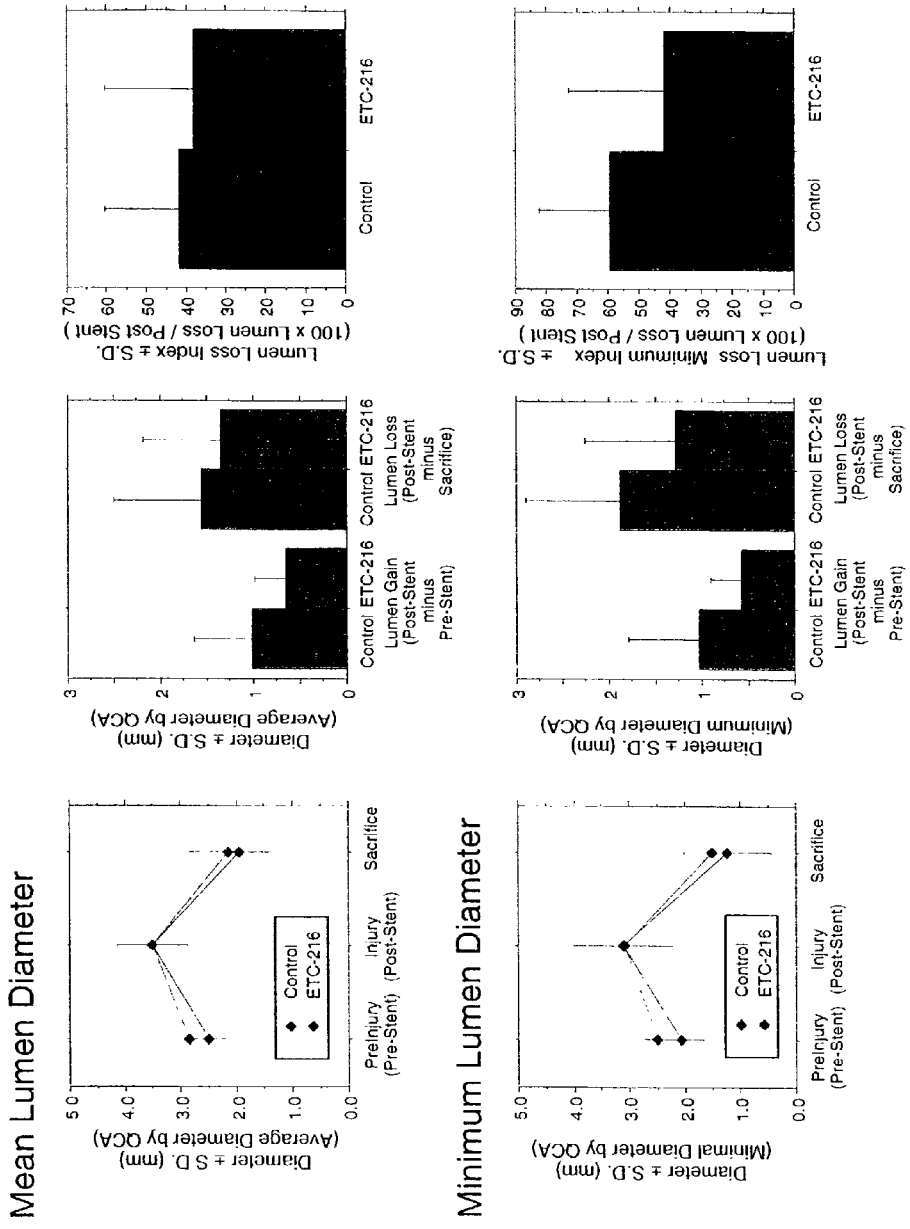
Figure 1a  Quantitative Coronary Angiography LAD and RCA (combined)

Effect of Single Dose ETC-216 Administration (100mg/kg) on IVUS Changes in Coronary Arteries in the Balloon Over-Inflated Stented Twenty-Eight Day Restenosis Pig Model Effect of Single Dose ETC-216 Administration (100mg/kg) on Histomorphometric Changes in Coronary Arteries in the Balloon Over-Inflated Stented Twenty-Eight Day Restenosis Pig Model Restenosis Correlation Variables of Coronary Arteries in Balloon Over-Inflated Stented Twenty-Eight Day Post-Injured Pigs Administered a Single Dose of ETC-216 (100mg/kg)

Effect of Intramural Dose ETC-216 Administration on Histomorphometric Changes in Coronary Arteries in the Balloon Over-Inflated Stented Twenty-Eight Day Restenosis

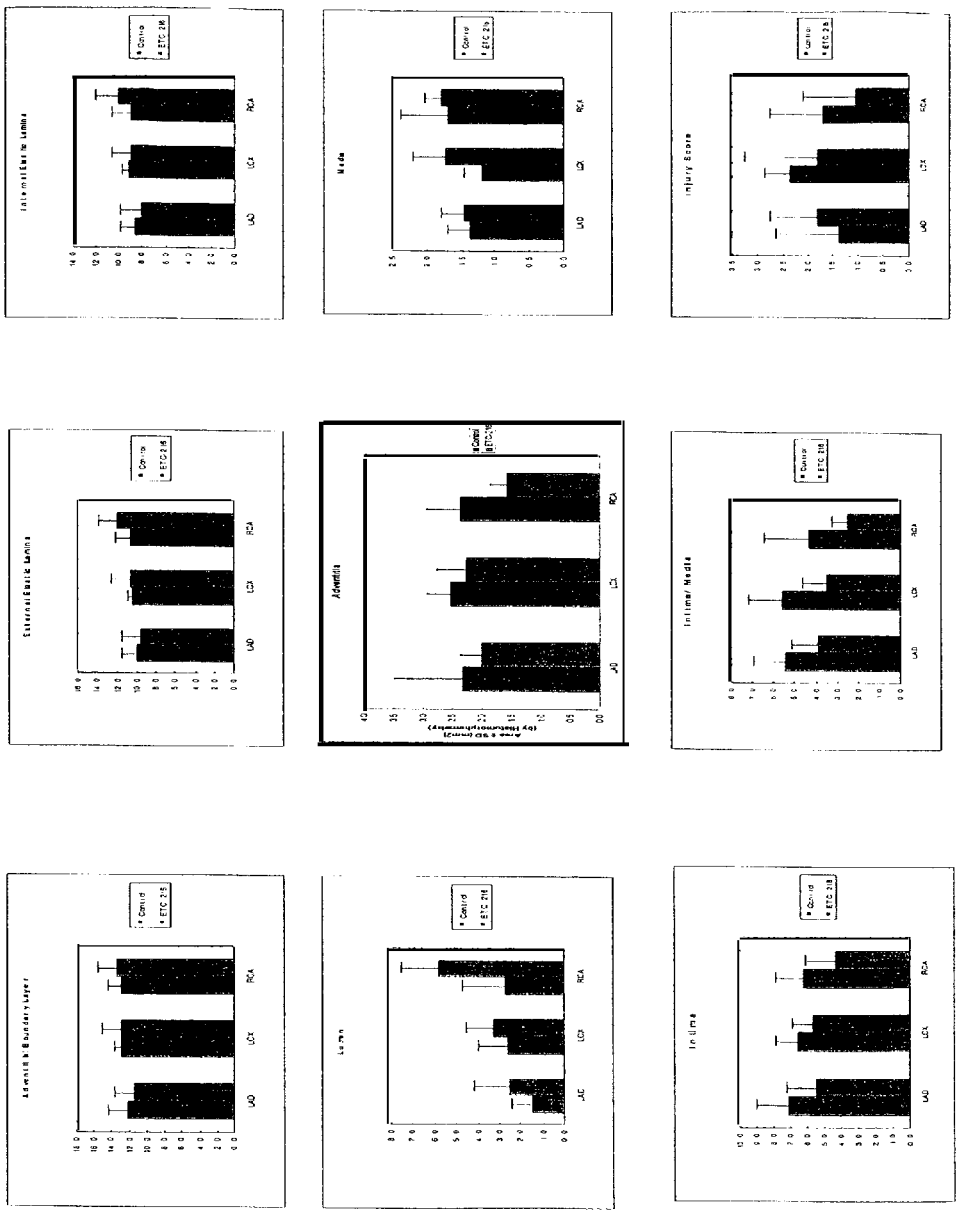
Figure 5b  Effect of Intramural Dose ETC-216 Administration on Histomorphometric Changes in Specific Coronary Arteries in the Balloon Over-Inflated Stented Twenty-Eight Day Restenosis Pig Model

SEQUENCE LISTING

<160> NUMBER OF SEQ ID NOS: 11

<210> SEQ ID NO 1
<211> LENGTH: 243
<212> TYPE: PRT
<213> ORGANISM: Homo sapiens (apolipoprotein A-I)

<400> SEQUENCE: 1

Asp Glu Pro Pro Gln Ser Pro Trp Asp Arg Val Lys Asp Leu Ala Thr
 1               5                  10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
 50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 2
<211> LENGTH: 243
<212> TYPE: PRT
<213> ORGANISM: Homo sapiens (apolipoprotein A-I Milano)

<400> SEQUENCE: 2

Asp Glu Pro Pro Gln Ser Pro Trp Asp Arg Val Lys Asp Leu Ala Thr
 1               5                  10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
 50                  55                  60

Gly Pro Val Thr Gln Glu Phe Trp Asp Asn Leu Glu Lys Glu Thr Glu

```
                65                  70                  75                  80
Gly Leu Arg Gln Glu Met Ser Lys Asp Leu Glu Glu Val Lys Ala Lys
                    85                  90                  95

Val Gln Pro Tyr Leu Asp Asp Phe Gln Lys Lys Trp Gln Glu Glu Met
                    100                 105                 110

Glu Leu Tyr Arg Gln Lys Val Glu Pro Leu Arg Ala Glu Leu Gln Glu
                    115                 120                 125

Gly Ala Arg Gln Lys Leu His Glu Leu Gln Glu Lys Leu Ser Pro Leu
            130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Cys Leu Ala Ala
                    165                 170                 175

Arg Leu Glu Ala Leu Lys Glu Asn Gly Gly Ala Arg Leu Ala Glu Tyr
                    180                 185                 190

His Ala Lys Ala Thr Glu His Leu Ser Thr Leu Ser Glu Lys Ala Lys
                    195                 200                 205

Pro Ala Leu Glu Asp Leu Arg Gln Gly Leu Leu Pro Val Leu Glu Ser
            210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 3
<211> LENGTH: 243
<212> TYPE: PRT
<213> ORGANISM: Homo sapiens (apolipoprotein A-I Paris)

<400> SEQUENCE: 3

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
                20                  25                  30

Phe Glu Gly Ser Ala Leu Gly Lys Gln Leu Asn Leu Lys Leu Leu Asp
            35                  40                  45

Asn Trp Asp Ser Val Thr Ser Thr Phe Ser Lys Leu Arg Glu Gln Leu
50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                    85                  90                  95

Val Gln Pro Tyr Leu Asp Asp Phe Gln Lys Lys Trp Gln Glu Glu Met
                    100                 105                 110

Glu Leu Tyr Arg Gln Lys Val Glu Pro Leu Arg Ala Glu Leu Gln Glu
                    115                 120                 125

Gly Ala Arg Gln Lys Leu His Glu Leu Gln Glu Lys Leu Ser Pro Leu
            130                 135                 140

Gly Glu Glu Met Arg Asp Cys Ala Arg Ala His Val Asp Ala Leu Arg
145                 150                 155                 160

Thr His Leu Ala Pro Tyr Ser Asp Glu Leu Arg Gln Arg Leu Ala Ala
                    165                 170                 175

Arg Leu Glu Ala Leu Lys Glu Asn Gly Gly Ala Arg Leu Ala Glu Tyr
                    180                 185                 190

His Ala Lys Ala Thr Glu His Leu Ser Thr Leu Ser Glu Lys Ala Lys
                    195                 200                 205
```

```
Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 4
<211> LENGTH: 299
<212> TYPE: PRT
<213> ORGANISM: Homo spaiens (apolipoprotein E)

<400> SEQUENCE: 4

Lys Val Glu Gln Ala Val Glu Thr Glu Pro Glu Pro Glu Leu Arg Gln
  1               5                  10                  15

Gln Thr Glu Trp Gln Ser Gly Gln Arg Trp Glu Leu Ala Leu Gly Arg
             20                  25                  30

Phe Trp Asp Tyr Leu Arg Trp Val Gln Thr Leu Ser Glu Gln Val Gln
         35                  40                  45

Glu Glu Leu Leu Ser Ser Gln Val Thr Gln Glu Leu Arg Ala Leu Met
 50                  55                  60

Asp Glu Thr Met Lys Glu Leu Lys Ala Tyr Lys Ser Glu Leu Glu Glu
 65                  70                  75                  80

Gln Leu Thr Pro Val Ala Glu Glu Thr Arg Ala Arg Leu Ser Lys Glu
                 85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Phe Gln Ala Arg Leu Lys Ser Trp Phe Glu Pro Leu Val Glu Asp Met
            260                 265                 270

Gln Arg Gln Trp Ala Gly Leu Val Glu Lys Val Gln Ala Ala Val Gly
        275                 280                 285

Thr Ser Ala Ala Pro Val Pro Ser Asp Asn His
    290                 295

<210> SEQ ID NO 5
<211> LENGTH: 267
<212> TYPE: PRT
<213> ORGANISM: Homo sapiens (proapolipoprotein A-I)
```

<400> SEQUENCE: 5

```
Met Lys Ala Ala Val Leu Thr Leu Ala Val Leu Phe Leu Thr Gly Ser
  1               5                  10                  15

Gln Ala Arg His Phe Trp Gln Gln Asp Glu Pro Pro Gln Ser Pro Trp
             20                  25                  30

Asp Arg Val Lys Asp Leu Ala Thr Val Tyr Val Asp Val Leu Lys Asp
         35                  40                  45

Ser Gly Arg Asp Tyr Val Ser Gln Phe Glu Gly Ser Ala Leu Gly Lys
     50                  55                  60

Gln Leu Asn Leu Lys Leu Leu Asp Asn Trp Asp Ser Val Thr Ser Thr
 65                  70                  75                  80

Phe Ser Lys Leu Arg Glu Gln Leu Gly Pro Val Thr Gln Glu Phe Trp
                 85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
                260                 265
```

<210> SEQ ID NO 6
<211> LENGTH: 77
<212> TYPE: PRT
<213> ORGANISM: Homo sapiens (apolipoprotein A-II)

<400> SEQUENCE: 6

```
Gln Ala Lys Glu Pro Cys Val Glu Ser Leu Val Ser Gln Tyr Phe Gln
  1               5                  10                  15

Thr Val Thr Asp Tyr Gly Lys Asp Leu Met Glu Lys Val Lys Ser Pro
             20                  25                  30

Glu Leu Gln Ala Glu Ala Lys Ser Tyr Phe Glu Lys Ser Lys Glu Gln
         35                  40                  45

Leu Thr Pro Leu Ile Lys Lys Ala Gly Thr Glu Leu Val Asn Phe Leu
     50                  55                  60

Ser Tyr Phe Val Glu Leu Gly Thr Gln Pro Ala Thr Gln
 65                  70                  75
```

<210> SEQ ID NO 7
<211> LENGTH: 100
<212> TYPE: PRT

<213> ORGANISM: Homo sapiens (proapolipoprotein A-II)

<400> SEQUENCE: 7

Met Lys Leu Leu Ala Ala Thr Val Leu Leu Leu Thr Ile Cys Ser Leu
1               5                   10                  15

Glu Gly Ala Leu Val Arg Arg Gln Ala Lys Glu Pro Cys Val Glu Ser
            20                  25                  30

Leu Val Ser Gln Tyr Phe Gln Thr Val Thr Asp Tyr Gly Lys Asp Leu
        35                  40                  45

Met Glu Lys Val Lys Ser Pro Glu Leu Gln Ala Glu Ala Lys Ser Tyr
    50                  55                  60

Phe Glu Lys Ser Lys Glu Gln Leu Thr Pro Leu Ile Lys Lys Ala Gly
65                  70                  75                  80

Thr Glu Leu Val Asn Phe Leu Ser Tyr Phe Val Glu Leu Gly Thr Gln
                85                  90                  95

Pro Ala Thr Gln
            100

<210> SEQ ID NO 8
<211> LENGTH: 376
<212> TYPE: PRT
<213> ORGANISM: Homo sapiens (apolipoprotein A-IV)

<400> SEQUENCE: 8

Glu Val Ser Ala Asp Gln Val Ala Thr Val Met Trp Asp Tyr Phe Ser
1               5                   10                  15

Gln Leu Ser Asn Asn Ala Lys Glu Ala Val Glu His Leu Gln Lys Ser
            20                  25                  30

Glu Leu Thr Gln Gln Leu Asn Ala Leu Phe Gln Asp Lys Leu Gly Glu
        35                  40                  45

Val Asn Thr Tyr Ala Gly Asp Leu Gln Lys Lys Leu Val Pro Phe Ala
    50                  55                  60

Thr Glu Leu His Glu Arg Leu Ala Lys Asp Ser Glu Lys Leu Lys Glu
65                  70                  75                  80

Glu Ile Gly Lys Glu Leu Glu Glu Leu Arg Ala Arg Leu Leu Pro His
                85                  90                  95

Ala Asn Glu Val Ser Gln Lys Ile Gly Asp Asn Leu Arg Glu Leu Gln
            100                 105                 110

Gln Arg Leu Glu Pro Tyr Ala Asp Gln Leu Arg Thr Gln Val Asn Thr
        115                 120                 125

Gln Ala Glu Gln Leu Arg Arg Gln Leu Thr Pro Tyr Ala Gln Arg Met
    130                 135                 140

Glu Arg Val Leu Arg Glu Asn Ala Asp Ser Leu Gln Ala Ser Leu Arg
145                 150                 155                 160

Pro His Ala Asp Glu Leu Lys Ala Lys Ile Asp Gln Asn Val Glu Glu
                165                 170                 175

Leu Lys Gly Arg Leu Thr Pro Tyr Ala Asp Glu Phe Lys Val Lys Ile
            180                 185                 190

Asp Gln Thr Val Glu Glu Leu Arg Arg Ser Leu Ala Pro Tyr Ala Gln
        195                 200                 205

Asp Thr Gln Glu Lys Leu Asn His Gln Leu Glu Gly Leu Thr Phe Gln
    210                 215                 220

Met Lys Lys Asn Ala Glu Glu Leu Lys Ala Arg Ile Ser Ala Ser Ala
225                 230                 235                 240

Glu Glu Leu Arg Gln Arg Leu Ala Pro Leu Ala Glu Asp Val Arg Gly
                245                 250                 255

```
Asn Leu Arg Gly Asn Thr Glu Gly Leu Gln Lys Ser Leu Ala Glu Leu
                260                 265                 270

Gly Gly His Leu Asp Gln Gln Val Glu Glu Phe Arg Arg Arg Val Glu
            275                 280                 285

Pro Tyr Gly Glu Asn Phe Asn Lys Ala Leu Val Gln Gln Met Glu Gln
    290                 295                 300

Leu Arg Gln Lys Leu Gly Pro His Ala Gly Asp Val Glu Gly His Leu
305                 310                 315                 320

Ser Phe Leu Glu Lys Asp Leu Arg Asp Lys Val Asn Ser Phe Phe Ser
                325                 330                 335

Thr Phe Lys Glu Lys Glu Ser Gln Asp Lys Thr Leu Ser Leu Pro Glu
                340                 345                 350

Leu Glu Gln Gln Gln Gln Gln Gln Glu Gln Gln Gln Glu Gln Val
            355                 360                 365

Gln Met Leu Ala Pro Leu Glu Ser
        370                 375

<210> SEQ ID NO 9
<211> LENGTH: 56
<212> TYPE: PRT
<213> ORGANISM: Homo sapiens (apolipoprotein C-I)

<400> SEQUENCE: 9

Pro Asp Val Ser Ser Ala Leu Asp Lys Leu Lys Glu Phe Gly Asn Thr
1               5                   10                  15

Leu Glu Asp Lys Ala Arg Glu Leu Ile Ser Arg Ile Lys Gln Ser Glu
            20                  25                  30

Leu Ser Ala Lys Met Arg Glu Trp Phe Ser Glu Thr Phe Gln Lys Val
        35                  40                  45

Lys Glu Lys Leu Lys Ile Asp Ser
    50                  55

<210> SEQ ID NO 10
<211> LENGTH: 79
<212> TYPE: PRT
<213> ORGANISM: Homo sapiens (apolipoprotein C-II)

<400> SEQUENCE: 10

Thr Gln Gln Pro Gln Gln Asp Glu Met Pro Ser Pro Thr Phe Leu Thr
1               5                   10                  15

Gln Val Lys Glu Ser Leu Ser Ser Tyr Trp Glu Ser Ala Lys Thr Ala
            20                  25                  30

Ala Gln Asn Leu Tyr Glu Lys Thr Tyr Leu Pro Ala Val Asp Glu Lys
        35                  40                  45

Leu Arg Asp Leu Tyr Ser Lys Ser Thr Ala Ala Met Ser Thr Tyr Thr
    50                  55                  60

Gly Ile Phe Thr Asp Gln Val Leu Ser Val Leu Lys Gly Glu Glu
65                  70                  75

<210> SEQ ID NO 11
<211> LENGTH: 79
<212> TYPE: PRT
<213> ORGANISM: Homo sapiens (apolipoprotein C-III)

<400> SEQUENCE: 11

Ser Glu Ala Glu Asp Ala Ser Leu Leu Ser Phe Met Gln Gly Tyr Met
1               5                   10                  15

Lys His Ala Thr Lys Thr Ala Lys Asp Ala Leu Ser Ser Val Gln Glu
```

-continued

```
                20                  25                  30
Ser Gln Val Ala Gln Gln Ala Arg Gly Trp Val Thr Asp Gly Phe Ser
            35                  40                  45

Ser Leu Lys Asp Tyr Trp Ser Thr Val Lys Asp Lys Phe Ser Glu Phe
        50                  55                  60

Trp Asp Leu Asp Pro Glu Val Arg Pro Thr Ser Ala Val Ala Ala
65                  70                  75
```

PREVENTION AND TREATMENT OF RESTENOSIS BY LOCAL ADMINISTRATION OF DRUG This application claims priority to U.S. Ser. No. 60/326,379 filed Sep. 28, 2001.

BACKGROUND OF THE INVENTION

The present invention is generally in the area of methods and compositions to reduce restenosis after revascularization of diseased coronary, peripheral, and cerebral arteries, and stenosis or restenosis of surgically-placed bypass grafts or transplanted organs, specifically by local administration of an agent such as apolipoprotein A-I Milano alone or in combination with lipid formulations or other cholesterol lowering agents or lipid regulating agents.

Angioplasty, surgery and other vascular interventions are complicated by an accelerated arteriopathy characterized by rapid growth of cells into the lumen within a short period of time. This growth is often severe enough to jeopardize the blood flow to distal organs.

Vascular bypass surgery has been widely used to treat stenotic and occluded blood vessels, as when plaques develop on the surface of blood vessels in atherosclerosis. In bypass surgery, one or more healthy blood vessels are grafted into the stenotic/occluded vessels beyond the site of stenosis or occlusion to shunt blood around the stenotic or occluded vessel to re-establish a sufficient blood supply to the tissue whose blood supply is endangered by the stenosis or occlusion. This surgery often successfully revascularizes the endangered tissue.

Angioplasty has been developed as an alternative treatment to bypass surgery, especially in patients who have been diagnosed early in the development of stenosis or occlusion of blood vessels due to the abnormal laying down of plaque on the luminal wall of a blood vessel. Angioplasty typically involves guiding a catheter which is usually fitted with a balloon or expandable metal mesh to an artery region of stenosis or occlusion and the brief inflation, one or more times, of the balloon or wire mesh to push the obstructing intravascular material or plaque up against the endothelial wall of the vessel, thereby compressing and/or breaking apart the plaque and reestablishing blood flow. However, angioplasty treatment can injure the vessel, especially when the balloon is over inflated or the mesh overextended, causing a variety of undesirable results, such as denudation (removal) of the endothelial cell layer in the region of the angioplasty, dissection of part of the inner vessel wall from the remainder of the vessel with accompanying occlusion of the vessel, or rupture of the tunica intima layer of the vessel.

Injury of arteries in animals induces a process of vascular repair which eventually causes the artery to become narrowed. A thick new layer, or neointima, of smooth muscle cells and inflammatory cells grows within the blood vessel, encroaching on the lumen. This process in animals represents the process that occurs clinically after angioplasty, endovascular stent implantation, organ transplantation, or bypass surgery, which greatly limits the long term successes of these techniques for treating obstructive arterial disease. Animal models of arterial injury and neointimal hyperplasia have been used to study the cellular events which lead to restenosis in humans, to devise treatment strategies to suppress tissue growth in an attempt to reduce restenosis and enhance long term clinical results. Pigs are particularly useful as an animal model for restenosis in humans.

Attempts to limit stenosis or restenosis of blood vessels following revascularization have included administration of pharmacologic agents and technical approaches. No pharmaceutical agent has been clinically approved for the indication to prevent restenosis in humans. One technical approach, endovascular stent placement, has been shown to partially reduce restenosis in humans after coronary arterial intervention, as reported by Serruys, et al. N. E. J. Med. 1994; 331: 489-495 and Fischman, et al. N. E. J. Med. 1994; 331:496-501. Nevertheless, stents themselves remain susceptible to significant restenosis in 20-30% of cases.

Increased knowledge of the mechanisms underlying vascular repair has led to innovative proposals for agents to limit accelerated arteriopathies. Circulatory leukocytes, including monocytes, are known to be among the very first cells recruited to blood vessels as atherosclerosis begins. Once within diseased arterial walls, these cells may engulf cholesterol and other lipids, and may also produce substances that attract other cells, cause other cells to proliferate, or degrade matrix components. Each of these secondary effects may in turn promote greater intimal thickening and more severe narrowing or occlusion of the arterial lumen. A similar role for leukocytes in restenosis after revascularization has not been proven. Although leukocyte activation has been connected to restenosis in humans (Pietersma, et al. Circulation 1995; 91:1320-1325; Mickelson, et al., 1996 JACC 28(2):345-353; Inoue, et al., 1996 JACC 28(5):1127-1133) broad inhibition of inflammation, for example with glucocorticoids, after revascularization has not reduced restenosis in humans (Pepine et al., Circulation 1990; 81:1753-1761). This observation is reminiscent of studies using both broadly active and very specifically targeted treatments for preventing restenosis. Broad treatments, for example with heparin, have been limited by systemic toxicities and dosing limitations. Specific treatments, for example with molecular strategies, have failed to inhibit all of the redundant cellular and molecular pathways which activate and potentiate the vascular repair process.

Ameli, et al., Circulation 90(4):1935-41 (1994) reported that several epidemiological studies have shown an inverse relation between high-density lipoprotein (HDL) cholesterol levels and coronary heart disease and a similar inverse relation between HDL and restenosis after coronary balloon angioplasty. They conducted a study to determine whether HDL directly influences neointima formation, investigating the effect of recombinant apoA-I Milano (apoA-IM, a variant of human apoA-I with Arg-173 to Cys substitution), on intimal thickening after balloon injury in cholesterol-fed rabbits. Rabbits received intravenous injections of 40 mg of apoA-IM linked to a phospholipid carrier on alternate days, beginning 5 days before and continuing for 5 days after balloon injury of femoral and iliac arteries (a total dosage of 200 mg/animal, or about 11.4 mg/kg/dose). Three weeks after balloon injury, apoA-IM-treated rabbits had significantly reduced intimal thickness compared with the two control groups. The intima-to-media ratio was also significantly reduced by apoA-IM by ANOVA compared with the two controls. The fraction of intimal lesion covered by macrophages, as identified by immunohistochemistry using a macrophage-specific monoclonal antibody, was significantly less in apoA-IM-treated rabbits compared with carrier-treated animals (25.3+/−17% versus 59.4+/−12.3%, P<0.005). Aortic cholesterol content, did not differ significantly between apoA-IM-treated animals and carrier alone-treated controls. Unfortunately, unlike in pigs where the lesions are more human like, results obtained in rabbits have not been predictive of results in humans.

Accordingly, there is a need for compositions and methods of promoting healing of vascular tissue and controlling vascular muscle cell proliferation (hyperplasia) to prevent restenosis of blood vessels after angioplasty, vascular bypass, organ transplantation, or vascular disease, with minimal risk of rapid reocclusion.

It is therefore an object of the present invention to provide a method and compositions to reduce restenosis after revascularization of diseased coronary, peripheral, and cerebral arteries and stenosis or restenosis of surgically-placed bypass grafts or transplanted organs.

It is a further object of the present invention to provide a method which is a simple and effective means of gene transfer.

SUMMARY OF THE INVENTION

Apolipoprotein A-I (ApoA-I), preferably a variant form such as Apolipoprotein A-I Milano (ApoA-IM), alone or more preferably in combination with a lipid carrier such as phospholipids or other drug, can be administered locally before or during bypass surgery on diseased coronary, peripheral, and cerebral arteries, surgery to implant grafts or transplanted organs, or angioplasty, or to stabilize unstable plaques. In the preferred embodiment, ApoA-IM is administered using an INFILTRATOR, intramural delivery device and/or other sustained, controlled release means of administration of the ApoA-IM, so that an effective dose is administered at the site of injury. Based on a pig model using ApoA-IM, an effective dose for treatment or prevention of restenosis is in the range of from 0.2 to 0.4 mg ApoA-IM/kg delivered to the site to be treated, or more specifically between 4 and 6 mg ApoA-IM/vessel to be treated. The upper dosage for intramural administration by INFILTRATOR is limited by the viscosity of the solution. For example, the method cannot be used with a solution of ApoA-IM which is too viscous to pass through the pores of an INFILTRATOR. As demonstrated by the examples, an effective amount is in the range of 0.3 to 0.4 ml of a 14 mg/ml solution of ApoA-IM (which is equivalent to between 4 and 6 mg in a single dose/vessel segment or about a dose of about 0.2 mg/kg for each vessel treated in a 25 kg pig), preferably administered in combination with 1-palmitoyl-2-oleoyl phosphatidylcholine (POPC) at a ratio of about 1:1 by weight.

In an alternative embodiment, the apolipoprotein is not provided directly, but the gene encoding the apolipoprotein is provided. The gene is introduced into the blood vessel in a manner similar to that used for the protein, where the protein is then expressed. The technique can also be used for delivery of genes for treatment or prevention or restenosis or other cardiovascular diseases.

In yet another embodiment, stents are coated with apolipoproteins alone, apolipoproteins formulated with lipids, genetically engineered cells expressing the apolipoproteins, naked DNA coding for an apolipoprotein, or other drugs such as anti-proliferatives for local delivery to an injury site. This embodiment also includes instances whereby coatings are added in combination to stents to allow greater effectiveness. In a preferred embodiment, the system is used with combination therapy, with for local delivery of an agent such as an apolipoprotein in combination with systemic antihypertension therapy, lipid regulation and/or anticoagulation therapy. Examples of drugs that can be utilized include lipid regulating agents such as niacin, statins, and fibrates; agents for glycemic control; anti-hypertensive agents; and agents that prevent or delay blood coagulation or platelet aggregation such as where the agent is aspirin, IIb/IIIa inhibitors, cloprigel or heparin. Maximum benefit may be obtained using local delivery therapy with more than one combination—e.g. local delivery plus anticoagulation plus lipid regulation. These treatments could begin prior to, concurrent with or following local delivery. Preferably the systemic treatments would be begun prior to the local delivery procedure.

DETAILED DESCRIPTION OF THE DRAWINGS

FIGS. 1-4 relate to tests in which ten domestic pigs were treated once with a single intravenous infusion of 100 mg/kg ETC-216, an apoA-IM/POPC (approximately 1/1 by weight) complex (n=5) or saline (n=5). Test agents were administered intravenously over approximately 3 hours while undergoing overstretch percutaneous transluminal coronary angioplasty with stent deployment in two coronary vessels per animal. Dosage was based on the weight of the protein component of the complex. Animals were euthanized on day 28 (8 animals) or day 29 (one animal) following quantitative coronary angiography and intravascular ultrasound (IVUS), coronary arteries were perfused and fixed for histomorphometric analysis. One control animal expired on day 27, and only histomorphometric data was collected and used from this animal.

FIGS. 1$a$ and 1$b$ are graphs of the quantitative coronary angiographic data (QCA), which was determined at three time points, prior to coronary injury, immediately following coronary injuries and stent deployment, and prior to sacrifice, and are based on diameter measurements (mm) made at an unstented segment proximal to the stent, at the proximal section of the stent, an average area throughout the length of the stent, at the distal section of the stent, and at an unstented segment distal to the stent. From these data, maximum diameter and minimum diameter of the stented areas were determined. QCA estimation of lumen gain (luminal diameter post-injury minus pre-injury) and lumen loss (luminal diameter post-injury minus 28-29-day follow-up) were determined in the stented and adjacent unstented segments. The QCA data for all vessels (i.e. the right coronary artery (RCA) and left anterior descending artery (LAD) combined) are shown in FIG. 1$a$ and for vessel type (i.e. the RCA or the LAD) in FIG. 1$b$.

FIGS. 2$a$ and 2$b$ are graphs of the intravascular ultrasound (IVUS) data used to determine stent and lumen area at the distal, middle and proximal region of each stented coronary vessel prior to sacrifice (28-29 days post-surgery). The difference between these measurements is the neointimal area. FIG. 2$a$ is for all vessels (i.e. the RCA and LAD combined) and FIG. 2$b$ is for vessel type (i.e. the RCA or the LAD).

FIGS. 3$a$ and 3$b$ are the histomorphometric analysis of stented arteries used to determine the average cross sectional areas of the adventitial boundary layer (ABL), the external elastic lamina (EEL), the internal elastic lamina (IEL), the lumen (L), the adventitia (A), the media (M), the intima (I), the intima to media ratio (I/M) and an injury score. The injury score is the average of 36 determinations of injury consisting of twelve determinations in each of the proximal (a), middle (b) and distal (c) segments at the strut sites of the stented vessel. Injuries were scored either 0, 1, 2 or 3 with 0 indicating an intact IEL (i.e. no injury) and 3 indicating a ruptured EEL with exposure to the adventitia (i.e. most severe injury). FIG. 3$a$ is the histomorphometric data for all vessels (i.e. the RCA and LAD combined) and FIG. 3$b$ is the histomorphometric data for vessel type (i.e. the RCA or the LAD).

Figure 4:
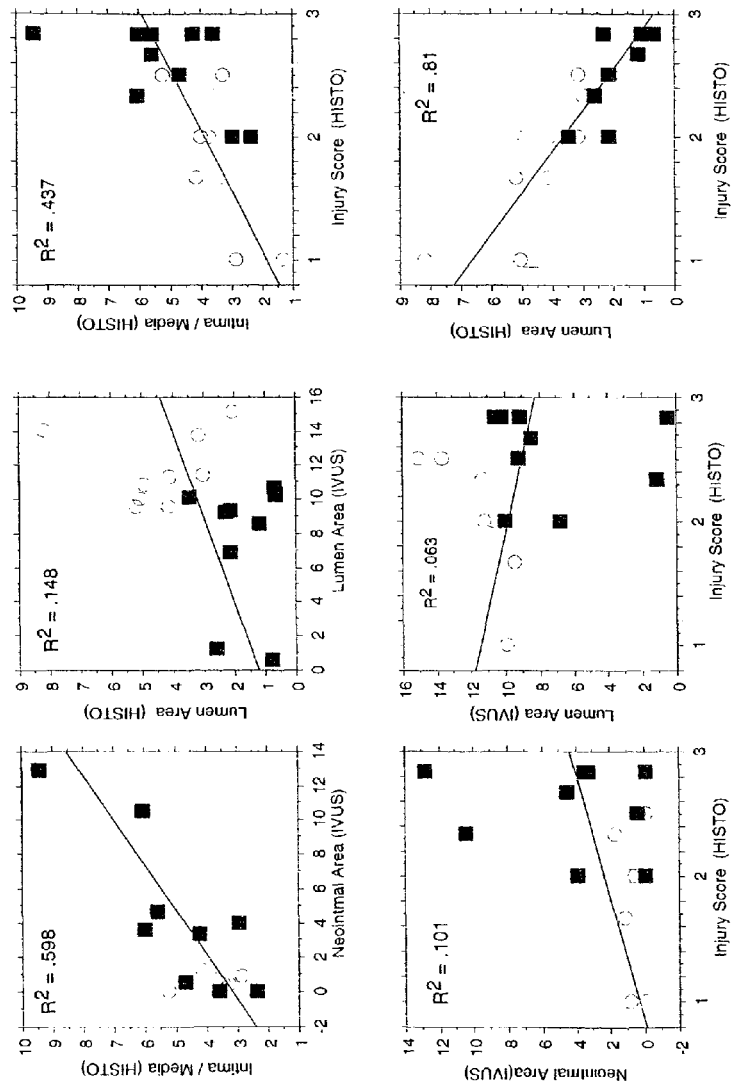

FIG. 4 shows select correlations between histomorphometric and IVUS variables.

Figure 5A:
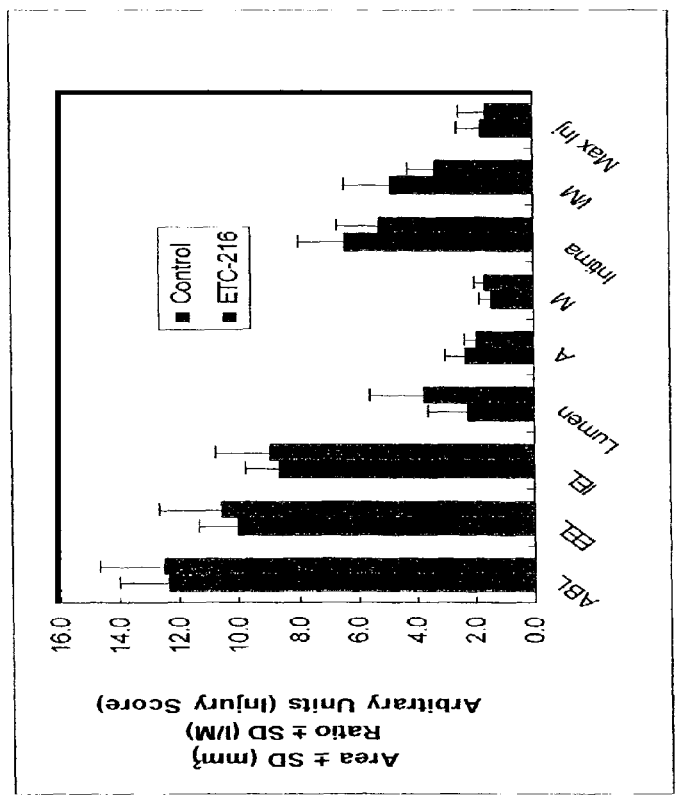

FIGS. 5$a$ and $b$ show the histomorphometric data collected from domestic pigs administered a 0.3-0.4 ml solution containing 4-6 mg protein/vessel ETC-216, an apoA-IMPOPC (~1/1 by weight) complex (n=6 pigs) or sucrose-mannitol vehicle (n=6 pigs) using an INFILTRATOR®, an intramural delivery device, with subsequent overstretch percutaneous transluminal coronary angioplasty with stent deployment in two coronary vessels per animal. Dose represents the weight of the protein component in the complex. Shown are the histomorphometric analysis of stented arteries used to determine the average cross sectional areas of the adventitial boundary layer (ABL), the external elastic lamina (EEL), the internal elastic lamina (IEL), the lumen (L), the adventitia (A), the media (M), the intima (I), the intima to media ratio (I/M) and the injury score. The injury score is the average of 36 determinations of injury consisting of twelve determinations in each of the proximal (a), middle (b) and distal (c) segments at the strut sites of the stented vessel. Injuries were scored either 0, 1, 2 or 3 with 0 indicating an intact IEL (i.e. no injury) and 3 indicating a ruptured EEL with exposure to the adventitia (i.e. most severe injury). The histomorphometric data of all vessels (i.e. the RCA, left circumflex (LCX) and LAD combined) is shown in FIG. 5a and by vessel type individually (i.e. the RCA, LCX or the LAD) is shown in FIG. 5b.

DESCRIPTION OF THE INVENTION

The system that has been developed is focused on the local application of a material that is useful in treating or preventing restenosis, locally before or during bypass surgery on diseased coronary, peripheral, and cerebral arteries, surgery to implant grafts or transplanted organs, or angioplasty, or to stabilize unstable plaques. The local administration is preferably achieved using a device that includes a reservoir that slowly releases drug over a period of time. The reservoir may be a part of the device, such as a stent, or created by injection into a particular tissue or organ, for example, via intrapericardial or INFILTRATOR administration. This can be done using commercially available cathethers.

The compositions to be administered may be cholesterol and oxidized lipid removing agents (such as apolipoproteins in combination with phospholipid, statins, fibrates), DNA encoding such agents (for example, encoding the apolipoproteins) or other proteins such as enzymes involved in nitric oxide generation, and/or drugs such as anti-proliferative compounds like rapamycin, paclitaxel or antibodies such as tirofiban and abciximab.

Combination therapy may also be used where drug such as ApoA-IM is administered locally and another drug is administered systemically, for example, systemic antihypertension therapy, lipid regulation and/or anti-coagulation therapy. Examples of drugs that can be utilized include lipid regulating agents such as niacin, statins, and fibrates; agents for glycemic control; anti-hypertensive agents; and agents that prevent or delay blood coagulation or platelet aggregation such as where the agent is aspirin, IIb/IIIa inhibitors, clopidogrel or heparin.

I. Lipid Modulating Agents

Apolipoprotein Formulations

Compounds which function as HDL include synthetic HDL which contains lipid such as phosphotidyl choline, phosphatidyl serine, phosphatidyl ethanolamine, and other phospholipids in combination with HDL associated proteins such as apoA-I or variants thereof including apoAI-Milano and biologically active peptides derived therefrom, reverse lipid transport (RLT) peptides, enzymes associated with HDL such as paraoxonase, and apo E, alone or formulated in combination with liposomes or emulsions. As used herein, HDL associated proteins include sequences present in HDL associated proteins that associate with HDL and synthetic peptides having equivalent binding or functional characteristics. Compounds which enhance HDL function include liposomes, where the HDL acts as a shuttle from the cells to the liposome. Suitable liposomal formulations are described in WO 95/23592 by the University of British Columbia.

The formulations described herein typically consist of an alpha helical protein such as an ApoA-I, a lipid, and a carrier.

ApoA-I and ApoA-IM are representative compositions that can be used to treat or prevent stenosis arising as a result of bypass surgery on diseased coronary, peripheral, and cerebral arteries, surgery to implant grafts or transplanted organs, or angioplasty.

Plasma ApoA-I (SEQ ID NO:1) is a singe polypeptide chain of 243 amino acids, whose primary sequence is known (Brewer et al., Biochem. Biophys. Res. Commun. 80:623-630 (1978)). ApoA-I is synthesized as a 267 amino acid precursor in the cell. This preproapolipoproteinA-I is first intracellularly processed by N-terminal cleavage of 18 amino acid to yield proapolipoproteinA-I (SEQ ID NO:5), and then further cleavage of 6 amino acids in the plasma or the lymph by the activity of specific proteases to yield apolipoproteinA-I. The major structural requirement of the ApoA-I molecule is believed to be the presence of repeat units of 11 to 22 amino acids, presumed to exist in amphipathic helical confirmation (Segrest et al., FEBS Lett 38:247-253 (1974)). This structure allows for the main biological activities of ApoA-I, i.e. lipid binding and lecithin-cholesterol acyltransferase (LCAT) activation.

Human apolipoprotein AI-Milano (ApoA-IM) (SEQ ID NO:2) is a natural variant of ApoA-I (Weisgraber et al., J. Clin. Invest. 66:901-907 (1980)). In ApoA-IM the amino acid Arg173 is replaced by the amino acid Cys173. Since ApoA-IM contains one Cys residue per polypeptide chain, it may exist in a monomeric, homodimeric, or heterodimeric form. These forms are chemically interchangeable, and the term ApoA-IM does not, in the present context, discriminate between these forms. On the DNA level, the variant form results from a C to T substitution in the gene sequence, i.e. the codon CGC changed to TGC, allowing the translation of a Cys instead of Arg at amino acid position 173. However, this variant of ApoA-I is one of the most interesting variants in that the ApoA-IM subjects are characterized by a remarkable reduction in HDL-cholesterol level, but without an apparent increased risk of arterial disease (Franceschini et al., J. Clin Invest 66:892-900 (1980)).

Another useful variant of ApoA-I is the Paris variant (SEQ ID NO:3), where Arg151 is replaced with Cys.

The systemic infusion of ApoA-I alone (Miyazaki et al. *Arterioscler Thromb Vasc Biol.* 15:1882-1888(1995) or of HDL (Badimon et al, *Lab Invest.* 60:455-461 (1989) and *J Clin Invest.* 85:1234-1241 (1990)) in experimental animals and initial human clinical studies (Nanjee et al., *Arterioscler Thromb Vasc Biol.* 19:979-989(1999) and Eriksson et al. *Circulation.* 100:594-598 (1999)) has been shown to exert significant biochemical changes, as well as to reduce the extent and severity of atherosclerotic lesions. It has now been discovered that it can be administered locally at a site of injury, and significantly reduce stenosis or restenosis, as discussed in more detail below and demonstrated by the following examples.

Other HDL-associated apolipoproteins with alpha-helical characteristics could be used. Examples include Apo E (SEQ ID NO:4), proApoA-I (SEQ ID NO:5), ApoA-IParis (SEQ ID NO:3), ApoA-II (SEQ ID NO:6), proapoA-II (SEQ ID NO:7), ApoA-IV (SEQ ID NO:8), ApoC-I (SEQ ID NO:9), ApoC-II (SEQ ID NO:10), and ApoC-III (SEQ ID NO:11), the alpha-helical sequences within these proteins, and apolipoproteins modified to include one or more sulfhydryl groups, as described by Bielicki and Oda, Biochemistry, 41:2089-2096 (2002)). Additional HDL-associated proteins can be used. Examples include paraoxonase, cholesteryl ester transfer protein, LCAT and phospholipid transfer protein. The above proteins can be used alone, in combination, complexed to lipid alone or in combination complexed to lipid. In addition, mixtures of complexes can be useful. An example is complexes comprised of ApoA-I with lipid and complexes comprised of paraoxonase with lipid administered as a mixture. Another example includes complexes comprised of greater than one protein component. For example, complexes comprised of ApoA-I, paraoxonase and lipid are useful.

Lipids

Lipids form a complex with the ApoA-I which enhances its efficacy. Typically, the lipid is mixed with the ApoA-I prior to administration. Apolipoprotein and lipids are mixed in an aqueous solution in appropriate ratios and can be complexed by methods known in the art and including freeze-drying, detergent solubilization followed by dialysis, microfluidization, sonication, and homogenization. Complex efficiency can be optimized, for example, by varying pressure, ultrasonic frequency, or detergent concentration. An example of a detergent commonly used to prepared apolipoprotein-lipid complexes is sodium cholate.

In some cases it is desirable to mix the lipid and the apolipoprotein prior to administration. Lipids may be in solution or in the form of liposomes or emulsions formed using standard techniques such as sonication or extrusion. Sonication is generally performed with a tip sonifier, such as a Branson tip sonifier, in an ice bath. Typically, the suspension is subjected to several sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Mass. or through a polycarbonate filter or other types of polymerized materials (i.e. plastics) commonly known.

In some cases it is preferable to administer the apolipopotein alone, essentially lipid-free, to treat the injured artery. The aqueous sterile solution is added to the apolipoprotein. The apolipoprotein in solution can be administered to treat an injured artery. Alternative, freeze-dried preparation of complexes may be hydrated with an aqueous solution prior to administration. In other cases, frozen preparations of complexes in aqueous solution are thawed until a homogenous solution is achieved prior to administration to an injured vessel, Preferred lipids are phospholipids, most preferably including at least one phospholipid, typically soy phosphatidylcholine, egg phosphatidylcholine, soy phosphatidylglycerol, egg phosphatidylglycerol, palmitoyl-oleoyl-phosphatidylcholine distearoylphosphatidylcholine, or distearoylphosphatidylglycerol. Other useful phospholipids include, e.g., phosphatidylcholine, phosphatidylglycerol, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, stearoyl-palmitoyl-phosphatidylcholine, di-palmitoylphosphatidylethanolamine, distearoyl-phosphatidylethanolamine, dimyrstoyl-phosphatidylserine, and dioleylphosphatidylcholine. Non-phosphorus containing lipids may also be used, including stearylamine, docecylamine, acetyl palmitate, and fatty acid amides.

Additional lipids suitable for use are well known to persons of skill in the art and are cited in a variety of well known sources, e.g., McCutcheon's Detergents and Emulsifiers and McCutcheon's Functional Materials, Allured Publishing Co., Ridgewood, N.J., both of which are incorporated herein by reference. Generally, it is desirable that the lipids are liquid-crystalline at 37° C., 35° C., or 32° C. Lipids in the liquid-crystalline state typically accept cholesterol more efficiently than lipids in the gel state. As patients typically have a core temperature of about 37° C., lipids that are liquid-crystalline at 37° C. are generally in a liquid-crystalline state during treatment.

The concentration of the lipid in the formulation may vary. Persons of skill may vary these concentrations to optimize treatment with different lipid components or of particular patients. ApoAI is combined with lipid in a ratio by weight of between 1:0.5 to 1:3, with more lipid being preferred for clearance of cholesterol. A ratio of around 1:1 is preferred to produce the most homogenous population and for purposes of producing stable and reproducible batches.

Other Lipid Modulating Drugs

Compounds can also be administered with compounds that increase HDL levels specifically (i.e., not as a byproduct of decreasing LDL), and thereby improve the HDL cholesterol to total cholesterol ratio, and administration of combinations of any of these which are effective to improve the HDL to total blood cholesterol levels.

Examples of drugs include lipid regulating agents such as niacin, statins, and fibrates.

Anti-Proliferative Drugs

The infiltrator can also be used for delivery of agents such as anti-proliferatives like paclitaxel and topotecan (*Biochemical Pharmacology,* 2001; 61(1):119-127).

Gene Delivery

In an alternative embodiment, genes encoding a protein to be delivered may be administered, rather than the protein. Gene transfer can be obtained using direct transfer of genetic material, in a plasmid or viral vector, or via transfer of genetic material in cells or carriers such as cationic liposomes. Such methods are well known in the art and readily adaptable for use in the gene mediated toxin therapies described herein. As reviewed by Francis, et al. Am. J. Pharmacogenomics 1(1): 55-66 (2001), gene therapy offers a novel approach for prevention and treatment of cardiovascular diseases. Technical advances in viral vector systems and the development of fusigenic liposome vectors have been crucial to the development of effective gene therapy strategies directed at the vasculature and myocardium in animal models. Gene transfer techniques are being evaluated as potential treatment alternatives for both genetic (familial hypercholesterolemia) and acquired occlusive vascular diseases (atherosclerosis, restenosis, arterial thrombosis) as well as for cardiac disorders including heart failure, myocardial ischemia, graft coronary arteriosclerosis and hypertension. See also, Teiger, et al., J. Cardiovasc. Pharmacol. 33(5):726-732 (1999).

Studies by Wolff et al., Biotechniques 11:474-85 (1991), demonstrate injection of naked DNA into muscle allows long term and low expression levels of proteins coded for within the DNA sequence. Administration of naked DNA to smooth muscle layers can be achieved by use of an intramural device, such as an INFILTRATOR® and allow expression of the proteins or their alpha helical domains to treat the injured vessel. Transfer vectors can be any nucleotide construction used to deliver genes into cells (e.g., a plasmid), or as part of a general strategy to deliver genes, e.g., as part of recombinant retrovirus or adenovirus (Ram et al. *Cancer Res.* 53:83-88, (1993)). Appropriate means for transfection, including viral vectors, chemical transfectants, or physico-mechanical methods such as electroporation and direct diffusion of DNA, are described by, for example, Wolff, J. A., et al., *Science,* 247, 1465-1468, (1990); and Wolff, J. A. *Nature,* 352, 815-818, (1991). As used herein, plasmid or viral vectors are agents that transport the gene into a cell without degradation and include a promoter yielding expression of the gene in the cell into which it is delivered. In a preferred embodiment vectors are derived from either a virus or a retrovirus. Preferred viral vectors are Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Preferred retroviruses include Murine Maloney Leukemia virus, MMLV, and retroviruses that express the desirable properties of MMLV as a vector.

Retroviral vectors are able to carry a larger genetic payload, i.e., a transgene or marker gene, than other viral vectors, and for this reason are a commonly used vector. However, they are not useful in non-proliferating cells. A retrovirus is an animal virus belonging to the virus family of Retroviridae, including any types, subfamilies, genus, or tropisms. Retroviral vectors, in general, are described by Verma, I. M., Retroviral vectors for gene transfer. In M-sc ICROBIOLOGY-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (*Science* 260:926-932 (1993)).

Adenovirus vectors are relatively stable and easy to work with, have high titers, and can be delivered in aerosol formulation, and can transfect non-dividing cells. The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992); Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, *Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970); Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); Wickham et al., *Cell* 73:309-319 (1993)).

Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors have higher transaction (ability to introduce genes) abilities than do most chemical or physical methods to introduce genes into cells. Typically, viral vectors contain nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines that have been engineered to express the gene products of the early genes in trans.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements. Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273:113 (1978)). The immediate early promoter of the human cytomegalovirus is conveniently obtained as a HindIII E restriction fragment (Greenway, P. J. et al., *Gene* 18:355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78:993 (1981)) or 3' (Lusky, M. L., et al., *Mol. Cell Bio.* 3:1108 (1983)) to the transcription unit. Furthermore, enhancers can be within an intron (Banerji, J. L. et al., *Cell* 33:729 (1983)) as well as within the coding sequence itself (Osborne, T. F., et al., *Mol. Cell Bio.* 4:1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

It is preferred that the promoter and/or enhancer region act as a constitutive promoter and/or enhancer to maximize expression of the region of the transcription unit to be transcribed. It is further preferred that the promoter and/or enhancer region be active in all eukaryotic cell types. A preferred promoter of this type is the CMV promoter (650 bases). Other preferred promoters are SV40 promoters, cytomegalovirus (full length promoter), and retroviral vector LTF. It has been shown that all specific regulatory elements can be cloned and used to construct expression vectors that are selectively expressed in specific cell types.

Expression vectors used in eukaryotic host cells may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In a preferred embodiment of the transcription unit, the polyadenylation region is derived from the SV40 early polyadenylation signal and consists of about 400 bases. It is also preferred that the transcribed units contain other standard sequences alone or in combination with the above sequences improve expression from, or stability of, the construct.

The viral vectors can include nucleic acid sequence encoding a marker product. This marker product is used to determine if the gene has been delivered to the cell and once delivered is being expressed. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure.

In a preferred embodiment, intramural delivery of DNA coding for ApoA-I, ApoA-IV, ApoE, paraoxonase or alpha-helical regions within these proteins are delivered to an artery with or with out lipid to treat injured blood vessels.

DNA encoding a number of different proteins may also be delivered. For example, as described by Chen, et al., Jpn. J. Pharmacol. 89(4):327-336 (2002), cardiovascular gene transfer is not only a powerful technique for studying the function of specific genes in cardiovascular biology and pathobiology, but also a promising strategy for treating cardiovascular diseases. Since the mid-1990s, nitric oxide synthase (NOS), the enzyme that catalyzes the formation of nitric oxide (NO) from L-arginine, has received considerable attention as a potential candidate for cardiovascular gene therapy, because NO exerts critical and diverse functions in the cardiovascular system, and abnormalities in NO biology are apparent in a number of cardiovascular disease processes including cerebral vasospasm, atherosclerosis, postangioplasty restenosis, transplant vasculopathy, hypertension, diabetes mellitus, impotence and delayed wound healing. There are three NOS isoforms, i.e., endothelial (eNOS), neuronal (nNOS) and inducible (iNOS). All three NOS isoforms have been used in cardiovascular gene transfer studies with encouraging results.

Kipshidze, et al., J. Am. Coll. Cardio. 39(10):1686-1691 (2002) describes decreasing neointimal formation by intramural delivery of antisense oligonucleotides.

Turunen, et al., Mol Ther 6(3):306 (2002), describes gene therapy with nuclear targeted lacZ- and TIMP-1-encoding adenoviruses were coupled to a peptide-motif (HWGF) that can bind to matrix metalloproteinase (MMP)-2 and MMP-9. In vivo, local intravascular catheter-mediated gene transfer of a HWGF-targeted TIMP-1-encoding adenovirus (AdTIMP-1(HWGF)) significantly reduced intimal thickening in a rabbit aortic balloon denudation model compared with the control adenovirus.

The advantage of the method disclosed herein is that it provides for delivery and release over a much longer time period at the site in need of treatment.

Drugs for Systemic Treatment

A variety of different drugs can be administered systemically and/or locally. These include agents for glycemic control; anti-hypertensive agents; anti-inflammatory agents such as steroidal anti-inflammatory agents, cyclooxygenase-2 (COX-2) inhibitors, such as Celebrex, VIOXX, and cyclooxygenase inhibitors like ibuprofen and other nonsteroidal anti-inflammatory agents, and agents that prevent or delay blood coagulation or platelet aggregation such as where the agent is aspirin, IIb/IIIa inhibitors, clopidogrel or heparin.

Stent Coatings

The stents may also be coated with apolipoproteins alone, apolipoproteins formulated with lipids, cells expressing the apolipoproteins or other proteins, DNA encoding the therapeutic proteins, or drugs having a local effect, such as paclitaxel, rapamycin or other anti-proliferative compounds. The coatings then release drug at the site of the injury, plaque, or area to be treated.

Pharmaceutically Acceptable Carriers

The pharmaceutical compositions typically include a pharmaceutically acceptable carrier. Many pharmaceutically acceptable carriers may be employed. The examples utilize sucrose-mannitol. Generally, normal saline will be employed as the pharmaceutically acceptable carrier. Other suitable carriers include glucose, trehalose, sucrose, sterile water, buffered water, 0.4% saline, and 0.3% glycine, and can further include glycoproteins for enhanced stability, such as albumin, apolipoprotein, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, and tonicity adjusting agents, for example, sodium acetate, sodium lactate, sodium chloride, potassium chloride, and calcium chloride.

In another embodiment, the ApoA-I is administered in a gel, or a polymer solution that forms a gel at the site of administration. In one embodiment, calcium alginate and certain other polymers that can form ionic hydrogels which are malleable. For example, a hydrogel can be produced by cross-linking the anionic salt of alginic acid, a carbohydrate polymer isolated from seaweed, with calcium cations, whose strength increases with either increasing concentrations of calcium ions or alginate. The alginate solution is mixed with the ApoA-I to form an alginate suspension which is injected directly into a patient prior to hardening of the suspension. The suspension then hardens over a short period of time due to the presence in vivo of physiological concentrations of calcium ions. Modified alginate derivatives, for example, more rapidly degradable or which are derivatized with hydrophobic, water-labile chains, e.g., oligomers of (-caprolactone, may be synthesized which have an improved ability to form hydrogels. Additionally, polysaccharides which gel by exposure to monovalent cations, including bacterial polysaccharides, such as gellan gum, and plant polysaccharides, such as carrageenans, may be crosslinked to form a hydrogel using methods analogous to those available for the crosslinking of alginates described above. Additional examples of materials which can be used to form a hydrogel include polyphosphazines and polyacrylates, which are crosslinked ionically, or block copolymers such as Pluronics™ or Tetronics™, polyethylene oxide-polypropylene glycol block copolymers which are crosslinked by temperature or pH, respectively. Other materials include polymers such as polyvinylpyrrolidone, hyaluronic acid and collagen. Polymers such as polysaccharides that are very viscous liquids or are thixotropic, and form a gel over time by the slow evolution of structure, are also useful. For example, hyaluronic acid, which forms an injectable gel with a consistency like a hair gel, may be utilized. Modified hyaluronic acid derivatives are particularly useful. Polymer mixtures also may be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) 100,000 can be combined to form a gel over the course of time, e.g., as quickly as within a few seconds.

Covalently crosslinkable hydrogel precursors also are useful. For example, a water soluble polyamine, such as chitosan, can be cross-linked with a water soluble diusothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, polymers may be utilized which include substituents which are crosslinked by a radical reaction upon contact with a radical initiator. For example, polymers including ethylenically unsaturated groups which can be photochemically crosslinked may be utilized, as disclosed in WO 93/17669. Additionally, water soluble polymers which include cinnamoyl groups which may be photochemically crosslinked may be utilized, as disclosed in Matsuda et al., ASAID Trans., 38:154-157 (1992).

The gel material is applied either by spraying (in an open procedure) or by use of the INFILTRATOR or catheter (during a closed procedure). Typically, the ApoA-I alone, ApoA-I in combination with the lipid, or ApoA-I complexed with lipid is mixed with these gels at the time of solidification or polymerization, and then diffuses slowly out at the surface of the vessel being treated.

In another embodiment, the pharmaceutically acceptable carrier is coated on a stent. The carrier can be selected to release the invention in a time dependent fashion. Persons of skill may vary the carriers to achieve optimized stent coatings to achieve time dependent release of the invention from the stent.

II. Methods of Treatment

In the principle embodiment, a cholesterol-lowering agent such as Apolipoprotein A-I (ApoA-I), preferably a variant form such as Apolipoprotein A-I Milano (ApoA-IM), alone or more preferably in combination with a lipid carrier such as phospholipids or another drug, is administered locally using a reservoir device such as an INFILTRATOR® before or during bypass surgery on diseased coronary, peripheral, and cerebral arteries, surgery to implant grafts or transplanted organs, or angioplasty, or to stabilize unstable plaques, so that an effective dose is administered at the site of injury. In other embodiments, the same techniques and materials are administered to reduce the consequence of plaque rupture including thrombus formation and ischemia.

In other preferred embodiments, the local therapy is initiated in combination with systemic therapy, for example, in combination with agents to reduce restenosis, decrease or prevent plaque rupture, lower blood cholesterol, lower atherosclerotic lesion cholesterol, reduce blood coagulation, regulate one or more of the blood lipids (i.e., lipid-regulating agent), reduce inflammation, or control blood pressure. Examples of drugs that can be utilized include lipid regulating agents such as niacin, statins, and fibrates; agents for glycemic control; anti-hypertensive agents; and agents that prevent or delay blood coagulation or platelet aggregation such as where the agent is aspirin, IIb/IIIa inhibitors, clopridogrel or heparin. These additional agents will typically be administered systemically at their normal therapeutic dosages.

Maximum benefit may be obtained using local delivery therapy with more than one combination—e.g. local delivery plus anticoagulation plus lipid regulation. These treatments can begin prior to, concurrent with or following local delivery. Preferably the systemic treatments would be begun prior to the local delivery procedure.

In the preferred embodiment, an Apo A-I formulation is administered by means of an intramural delivery device, such as the INFILTRATOR available from Intraventional Technologies, Inc, San Diego, Calif., now owned by Boston Scientific. Another useful device is described by Pavlides, et al., Cathet. Cardiovasc. Diagn. 41(3):287-292 (1997). Other means of delivery can utilize catheters delivering the drug from a reservoir, either prior to angioplasty, during or after inflation of the balloon.

In the most preferred embodiment, an ApoA-IM formulation is administered in a single dose prior to or at the time of treatment. Treatments include angioplasty, bypass surgery of diseased coronary, peripheral, or cerebral arteries, implantation of vascular stents, implantation of transplanted organs or tissues, and stabilization of plaques.

The preferred dosage is determined through experimental studies, as was done in the following examples for ApoA-IM. Dosages for other apolipoproteins can be readily calculated based on the dosages for ApoA-IM, taking into account the differences in efficiency of cholesterol removal, half-lives, and other relevant pharmacokinetic parameters. Alternatively, the dosage for other apolipoproteins can be readily calculated by taking into account the differences in efficiency of the anti-oxidant, anti-inflammatory and antiantithrombotic properties of the preparations. The presence and amount of lipid can be similarly determined for the different formulations based on the experimental data obtained for ApoA-IM.

In general, the formulation is administered at the site of treatment. The actual total dosage when delivered locally is significantly less than the dosage that would have to be administered systemically to achieve the same local dosage, however, the local concentration is much higher than the previous studies in which the ApoA-I was administered systemically. As noted above, the preferred dosages for ApoA-IM are between 4 and 6 mg ApoA-IM/vessel (typically up to three segments are treated with a total dosage of around 4 to 18 mg ApoA-IM), or between about 0.05 and 0.3 mg ApoA-IM/kg body weight in a 70 kg mammal. The preferred ratio of protein to lipid is between 1:0.5 to 1:3, with more lipid being preferred for clearance of cholesterol, but a more equal amount of protein to lipid being preferred for purposes of stability and consistency of preparations for regulatory approval. Ratios of protein to lipid for preparations other than those containing apoA-IM are tested at various ratios of protein to lipid and the stability and consistency, and characteristics (such as complex size and cholesterol efflux capacity) are determined for regulatory approval.

Although a single administration has been demonstrated to be efficacious, multiple dosages can be administered. For example, intravenous administration at day −1, 0, 1, 2 and 3 of 20 mg ApoA-IM/kg body weight resulted in all balloon overstretched injured vessels showing increased lumen area relative to controls four weeks after the procedure.

The present invention will be further understood by reference to the following non-limiting examples.

Percutaneous coronary interventions are now a major method to increase the lumen of narrowed blood vessels in patients with coronary ischemia. These procedures are performed by percutaneous transluminal coronary angioplasty (PTCA), commonly known as "ballooning". In most cases, the procedure is completed with deployment of a stent to the dilated area with the goal of increasing the diameter of the blood vessel to increase blood flow and relieve ischemia. A major drawback is the post-procedural closure of the blood vessel lumen known as restenosis. In the absence of stents, the post-procedural incidence of early recoil and thrombosis are problematic, and therefore most balloon procedures today also include deployment of a stent. Although stenting improves outcome, post-procedural neointimal growth of a stented vessel can cause restenosis and recurrent ischemia or other coronary events, including myocardial infarction. Therefore, methods to prevent neointimal growth of ballooned and stented blood vessels are desired to improve procedural outcome. The porcine model was selected as the appropriate test system for the purposes of this study. Evidence in the literature suggests that arterial dilatation and restenosis in the porcine model is similar to that of human restenosis. Hence, this model can be used for evaluating potential therapeutic agents for the treatment of clinical restenosis.

EXAMPLE 1

Effect of Single High Dose Intravenous Delivery of ETC-216, a Preparation Containing Complexes Comprised of ApoA-IM and Palmitoyl-Oleoyl-Phosphatidylcholine (POPC) on Restenosis in Overstretch Percutaneous Transluminal Coronary Angioplasty (PTCA) with Stent Deployment in the Coronary Arteries of Pigs The objective of this study was to determine the effect of a single intravenous drug delivery of ETC-216 during coronary PTCA and stent placement on restenosis in a porcine model of vascular injury.

Materials and Methods

Experimental Animals

The porcine model was selected as the appropriate test system for the purposes of this study. Evidence in the literature suggests that arterial dilitation and restenosis in the porcine model is similar to that of human restenosis. Hence, this model can be used for evaluation potential therapeutic agents for the treatment of restenosis. Animals were acclimated to the laboratory environment for a minimum 7 days and examined prior to initiation of the study to ensure that they appear healthy.

During the quarantine and prior to surgery the animals were housed individually in runs. Animal pens were cleaned twice daily. The temperature and humidity in the animals' quarters (70-78 (F; 30-80% RH) were monitored to maintain a target range of 70-80° C. and 30-80 percent relative humidity. The airflow in the room was sufficient to provide several exchanges per hour with 100% fresh filtered air. An automatic timing device provided an alternating 12-hour cycle of light and dark. Following surgery animals were recovered in the recovery room, then returned to pens. Animals were fed once a day a meal of pig chow (Southwest Farms Hog Finisher Diet) obtained from Newco (Rancho Cucamonga, Calif.) throughout the experimental period, except on days of surgery, when animals were fasted overnight. Fresh water was supplied ad libitum via an automatic watering system.

Animals were randomly selected and assigned to two study groups. Additional animals were ordered for the study in the event that an animal died or had to be euthanized due to the surgical procedure or complications deemed to result from the surgical procedure.

Test substance consisted of either ETC-216, a recombinant apolipoprotein A-I Milano/1-palmitoyl-2oleoyl phosphatidylcholine (POPC) complex provided by Esperion Therapeutics, Inc., as a ready to inject solution or saline. ETC-216 solutions contain apoA-IM protein at about 14 mg/ml with a protein to POPC ratio of about 1 to 1 by weight. Intravenous administration was selected for this study, because it is the route intended for use in human clinical studies. The dose selection was based on animal body weight. Test substance were administered at a 100 mg/kg body weight dose. This dose was based on the apolipoprotein content of the complex. Thus, an average pig in the study would receive about 3000-3500 mg of drug. Control animals received saline.

Surgeries were performed in adult domestic swine (weighing approximately 30-35 kg, with one animal at 50 kg). Animals were fed normal diet and housed in the vivarium. Swine were fasted overnight and pretreated with oral aspirin, 325 mg, beginning 3 days prior to surgery and daily thereafter until euthanasia. Ticlopidine (250 mg) was given to animals beginning 3 days prior to surgery and daily for 14 days after surgery. After an overnight 16-hour fast, the animals were immobilized by an intramuscular (IM) injection of acepromazine (0.5 mg/kg), ketamine (20 mg/kg), and atropine (0.05 mg/kg); anesthesia was induced with intravenous (IV) thiopental (5-8 mg/kg); and maintained by 1-2% isoflurane after endotracheal intubation. Mechanical ventilation, arterial blood pressure (BP) and continuous electrocardiogram (ECG) monitoring were performed throughout the procedure. Animals were given cardizem (120 mg) daily for 2 days after surgery.

The surgical procedure consisted of exposure of a carotid artery followed by insertion of an 8F sheath into the carotid artery. The animals were given bretylium tosylate (250 mg IV), inderal (1 mg) and heparin (10,000 U IV) prior to coronary instrumentation. ETC-216 or saline was administered as an IV infusion commencing 90 minutes prior to the surgical procedure such that the entire dose was administered over approximately 3 hours. An 8F AL-0.75 guiding catheter was advanced to the ostia of the coronary arteries under fluoroscopic guidance. After administration of intracoronary nitroglycerin (200 mcg), angiography was performed in order to estimate the size of the vessel. Stent overstretch injury was performed in the first vessel, and then repeated in the second vessel. In all cases, stents were deployed in the LAD and RCA. Stents were deployed in the LAD and the RCA in segments averaging 2.7 to 3.0 mm in diameter using the location of diagonal or septal branches as anatomical reference. All stents were deployed using a balloon that was inflated one to three times to 6-8 atmospheres for 30 seconds to obtain a final stent: artery ratio of ~1.3:1. Angiography was performed initially to target stent site and repeated to confirm injury at stent deployment site as evidenced by an obvious "step-up" and a "step-down" of the injured segment. The catheters were withdrawn, the carotid artery ligated and the skin incision closed. As prophylaxis against infection, all animals received antibiotics at the end of the procedure. The animals were recovered from anesthesia, returned to the vivarium, fed a normal chow diet with additional medication as described above.

Angiographic and IVUS Measurements

Quantitative coronary angiography (QCA) was used to assess mean and minimum luminal diameter at various time points, i.e., pre-injury, immediately post-injury and at 28-29 days follow-up prior to euthanasia.

Definition of terms used during Quantitative Coronary Angiography:
MLD=mean lumen diameter
$R_1$=reference segment to proximal segment (unstented)
Prox.=proximal segment of the stented artery
Mid.=mid segment of the stented artery
Dist.=distal segment of the stented artery
$R_2$=reference segment to distal segment (unstented)
Max=maximum luminal diameter throughout the stented segment
Min=minimum luminal diameter throughout the stented segment
Lumen gain=Luminal diameter post injury minus pre injury
Lumen loss=Luminal diameter post injury minus 28 days follow-up Percent stenosis of the injured segments was estimated using the uninjured segments as reference. Stent area, lumen area, neointimal area, percent area stenosis parameters were measured by intravascular ultrasound (IVUS).

Late luminal loss was calculated as the difference in MLD immediately post-balloon injury and at 28-29 days follow-up, and the remodeling index was calculated as late luminal loss divided by post-injury MLD.

Analysis of Coronary Arteries at Follow-up

After 28 (n=8) or 29 (n=1) days, animals fasted overnight, were prepared for surgery as above, for follow-up angiography. (In one control saline-treated animal, that expired on day 27, only histology was performed). In addition, at follow-up, an IVUS catheter was deployed in the stented coronary arteries for IVUS study of each stented artery. Animals were then euthanized under anesthesia with IV pentobarbital 90 mg/kg, and hearts excised after thoracotomy. The coronary arteries were perfused with saline to clear the blood and then perfusion-fixed with 2% paraformaldehyde for 15 minutes followed by immersion in 4% paraformaldehyde in phosphate buffer (pH 7.4) for 4 hours and finally stored in 70% ethanol. To preserve the integrity of the adventitia and perivascular tissues, coronary arteries were carefully removed along with adjacent tissues (the adipose tissue and the myocardium). For stented segments, special histologic processing was performed to maintain the vascular architecture with metallic struts in situ. Tissue blocks were embedded in methyl methacrylate and cut with a diamond-wafering blade. Three radial cross sections containing 12 struts were cut: one from the proximal, one from the middle and one from the distal third of each stent. Sections were ground to a thickness of about 50 μm, optically polished, and stained with toluidine blue (paragon stain).

Histomorphometric Analysis

A computerized imaging system (Image Pro Plus 4.0) was used for histomorphometric measurements of:

1. The mean cross sectional area and lumen thickness (area circumscribed by the intima/neointimal-luminal border); neointimal (area between the lumen and the internal elastic lamina, IEL, and when the IEL is missing, the area between the lumen and the remnants of media or the external elastic lamina, EEL); media (area between the IEL and EEL); vessel size (area circumscribed by the EEL but excluding the adventitial area); and adventitia (area between the peri-adventitial tissues, adipose tissue and myocardium, and EEL).

2. The injury score. To quantify the degree of vascular injury, a score based on the amount and length of tear of the different wall structures was used. The degree of injury was calculated as follows:

0=intact IEL
1=ruptured IEL with exposure to superficial medial layers
2=ruptured IEL with exposure to deeper medial layers (medial dissection)
3=ruptured EEL with exposure to the adventitia Results Five domestic pigs treated with saline or five pigs treated with ETC-216 (Four males and one female pigs/group) were evaluated for post-treatment restenosis after 27-29 days.

Blood was obtained from some but not all animals over the course of the study for the determination of white blood cell count, red blood cell count, blood hemoglobin content, percent hematocrit, blood platelet counts. In all cases where these blood variables were determined, post-treatment values did not vary appreciably from the baseline values. That is, they were all within the normal range.

Heart rate and blood pressure were determined for all animals entered in the study at baseline. Heart rate and blood pressure were also periodically determined on most animals during the surgical procedures, and prior to sacrifice. For animals entered into the study these variables did not vary appreciably from baseline values due to either the surgical procedure or treatments.

Quantitative Coronary Angiography (QCA) was determined at three time points, prior to coronary injury, immediately following coronary injuries and stent deployment, and prior to sacrifice (FIG. 1a and FIG. 1b). Diameter measurements (mm) were made at an unstented segment proximal to the stent (R1), at the proximal section of the stent (Prox), an average area throughout the length of the stent (Aver), at the distal section of the stent (Dist), and at an unstented segment distal to the stent (R2). In addition, the maximum diameter (Max) and minimal diameter (Min) of the stented region were determined. QCA estimation of lumen gain and lumen loss were determined in the stented and adjacent unstented segments. Indexes for maximal (Lumen Loss Max Index) and minimal (Lumen Loss Min Index) of the stented vessels were determined. The quantitative coronary angiographic data for all vessels (i.e. the RCA and LAD combined) or vessel type (i.e. the RCA or the LAD) are shown graphically in FIGS. 1a and 1b, respectively.

Intravascular ultrasound (IVUS) was used to determine stent and lumen area at the distal, middle and proximal region of each stented coronary vessel prior to sacrifice The difference between these measurements is the neointimal area. The averages of stent, lumen and neointimal area for each animal and segment were determined, and used to determine averages for treatment groups of the pooled (LAD plus RCA) or the individual coronary vessels (LAD or RCA). One control-treated pig died one day prior to its schedule procedure (i.e. on day 27) and therefore only histomorphometric measurements were made on its stented coronary vessels. The intravascular ultrasound data for all vessels (i.e. the RCA and LAD combined) and for vessel type (i.e. the RCA or the LAD) are shown graphically in FIGS. 2a and 2b, respectively.

Histomorphometric analysis of stented arteries were used to determine the average cross sectional areas of the adventitial boundary layer (ABL), the external elastic lamina (EEL), the internal elastic lamina (IEL), the lumen (L), the adventitia (A), the media (M), the intima (I), the intima to media ratio (I/M) and an injury score. The injury score is the average of 36 determinations of injury consisting of twelve determinations in each of the proximal (a), middle (b) and distal (c) segments at the strut sites of the stented vessel. Injuries were scored either 0, 1, 2 or 3 with 0 indicating an intact IEL (i.e. no injury) and 3 indicating a ruptured EEL with exposure to the adventitia (i.e. most severe injury). ETC-216 treatment significantly reduced the intimal to media (I/M) ratio in coronary vessels by 32 percent (RCA and LAD combined). This effect was largely due to a significant 38 percent reduction of the I/M ratio of the LAD and to a lesser extent a 22 percent reduction (not significant) in the RCA. It should be noted the RCA was significantly more resilient to injury (injury score=1.87±0.54) than the LAD (injury score=2.57±0.34). The histomorphometric data for all vessels (i.e. the RCA and LAD combined) and for vessel type (i.e. the RCA or the LAD) are shown graphically in FIGS. 3a and 3b, respectively. Select correlation between histomorphometric and IVUS variables are shown in FIG. 4.

EXAMPLE 2

Effect of INFILTRATOR Intramural Delivery of ETC-216, a Preparation Containing Complexes Comprised of ApoA-IM and Palmitoyl-Oleoyl-Phosphatidylcholine (POPC) on Restenosis in Overstretch Percutaneous Transluminal Coronary Angioplasty (PTCA) with Stent Deployment in the Coronary Arteries of Pigs Materials and Methods Experiments were performed in adult domestic swine weighing 25-30 kg. Animals were fed a normal chow diet for pigs and housed in the vivarium. Swine were fasted overnight and pretreated with oral aspirin (325 mg) beginning 3 days prior to surgery and daily thereafter until euthanasia. Ticlopidine (250 mg) was given to animals beginning 3 days prior to surgery and daily for 14 days after surgery. Cardizem was given to animals (120 mg) daily for 2 days after surgery.

After an overnight 16 hour fast, the animals were immobilized by an intramuscular (IM) injection of acepromazine (0.5 mg/kg), ketamine (20 mg/kg), and atropine (0.05 mg/kg); anesthesia was induced with intravenous (IV) thiopental (5-8 mg/kg); and maintained by 1-2% isoflorane after endotracheal intubation. Mechanical ventilation, arterial blood pressure (BP) and continuous electrocardiogram (ECG) monitoring were performed throughout the procedure.

The surgical procedure consisted of exposure of a carotid artery and an 8F sheath inserted into the carotid artery. The animals were given bretylium tosylate (250 mg IV), inderal (1 mg IV) and heparin (8,000 U IV) prior to coronary instrumentation. An 8F AL-0.75 guiding catheter was advanced to the ostia of the coronary arteries under fluoroscopic guidance. After administration of intracoronary nitroglycerin (200 mcg), quantitative coronary angiography was performed for all three coronary arteries in order to estimate the size of the vessels. The two largest vessels were selected for the procedure. ETC-216 or sucrose-mannitol vehicle was administered intramurally via INFILTRATOR during the surgical procedure prior to PTCA with stent deployment. The INFILTRATOR catheter was introduced for the delivery of ETC-216 or sucrose-mannitol vehicle at a very low dose to the coronary vessel wall to minimize the loss of the agent into the circulation. Two arteries in each animal were infiltrated with 4-6 mg ETC-216 or sucrose-mannitol vehicle each in a dose volume of 0.3-0.4 ml. Thus each animal received a total dose of about 8-12 mg ETC-216 localized to two artery segments. Each artery underwent infiltration procedure by inflating the attached balloon once to 1.5-2 atmospheres in pressure during the delivery of ETC-216 or sucrose-mannitol vehicle prior to balloon over-inflation with stent deployment. Following the infiltration procedure, stents were deployed precisely in the infiltrated segments of LAD, RCA, and LCX, using the location of diagonal or septal branches as anatomical reference. All stents were deployed using a balloon that were inflated one to three times to 6-8 atmospheres for 30 seconds to obtain a final stent: artery ratio of ~1.3:1. Angiography was performed initially to target stent site and repeated to confirm injury at stent deployment site as evidenced by an obvious "step-up" and a "step-down" of the injured segment. The catheters were withdrawn, the carotid artery ligated and the skin incision closed. As prophylaxis against infection, all animals received antibiotics at the end of the procedure. The animals were recovered from anesthesia, returned to the vivarium, fed a normal chow diet with additional medication as described above.

Angiographic and IVUS Measurements

Quantitative coronary angiography (QCA) was used to assess mean and minimum luminal diameter at various time points, i.e., pre-injury, immediately post-injury and at 28 days follow-up prior to euthanasia. Late luminal loss was calculated as the difference in MLD immediately post-balloon injury and at 28 days follow-up, and the remodeling index was calculated as late luminal loss divided by post-injury MLD.

Definition of terms used during Quantitative Coronary Angiography:
R2=reference segment to proximal segment (unstented)
P=proximal segment of the stented artery
M=mid segment of the stented artery
D=distal segment of the stented artery
R2=reference segment to distal segment (unstented)
Max=maximum luminal diameter throughout the stented segment
Min=minimum luminal diameter throughout the stented segment
Lumen gain=Luminal diameter post injury minus pre injury
Lumen loss=Luminal diameter post injury minus 28 days follow-up Percent stenosis of the injured segments was estimated using the uninjured segments as reference. Stent area, lumen area, neointimal area, percent area stenosis (all IVUS) parameters were measured.

Analysis of Coronary Arteries at Follow-up

After 28 days, animals fasted overnight, were prepared for surgery as above, for follow-up angiography. In addition, at follow-up, an IVUS catheter was deployed in the stented coronary arteries for IVUS study of each stented artery. Animals were then euthanized under anesthesia with IV pentobarbital 90 mg/kg, and hearts excised after thoracotomy. The coronary arteries were perfused with saline to clear the blood and then perfusion-fixed with 2% paraformaldehyde for 15 minutes followed by immersion in 4% paraformaldehyde in phosphate buffer (pH 7.4) for 4 hours and finally stored in 70% ethanol. To preserve the integrity of the adventitia and perivascular tissues, coronary arteries were carefully removed along with adjacent tissues (the adipose tissue and the myocardium). For stented segments, special histologic processing was performed to maintain the vascular architecture with metallic struts in situ. Tissue blocks were embedded in methyl methacrylate and cut with a diamond-wafering blade. Three radial cross sections containing 12 struts were cut: one from the proximal, one from the middle and one from the distal third of each stent. Sections were ground to a thickness of about 50 um, optically polished, and stained with toluidine blue (paragon stain).

Histomorphometric Analysis

A computerized imaging system Image Pro Plus 4.0 was used for histomorphometric measurements of:
1. The mean cross sectional area and lumen thickness (area circumscribed by the intima/neointimal-luminal border); neointimal (area between the lumen and the internal elastic lamina, IEL, and when the IEL is missing, the area between the lumen and the remnants of media or the external elastic lamina, EEL); media (area between the IEL and EEL); vessel size (area circumscribed by the EEL but excluding the adventitial area); and adventitia (area between the periadventitial tissues, adipose tissue and myocardium, and EEL).
2. The injury score. To quantify the degree of vascular injury, a score based on the amount and length of tear of the different wall structures was used. The degree of injury was calculated as follows:

0=intact IEL
1=ruptured IEL with exposure to superficial medial layers
2=ruptured IEL with exposure to deeper medial layers (medial dissection)
3=ruptured EEL with exposure to the adventitia Results Two coronary arteries each from fourteen domestic pigs were treated with sucrose-mannitol vehicle (control) or 4-6 mg ETC-216 (n=7 per group). Quantitative coronary angiography (QCA) of the left anterior descending (LAD), the left circumflex (LCX) and the right coronary arteries (RCA) was performed in order to estimate the size of each vessel; the two largest arteries were selected for the procedure. In each artery, the drug was delivered intramurally via the INFILTRATOR followed by overstretch percutaneous transluminal coronary angioplasty (PTCA) with stent deployment at the site of drug delivery. This surgical procedure induced a vascular injury in which inflammation, neointimal hyperplasia and restenosis develops. The stented arteries from all animals were subjected to QCA prior to, immediately following stenting, and just prior to sacrifice at day 28. In addition, IVUS was used to determine stent and lumen area to estimate the neointimal area just prior to sacrifice. After sacrifice, segments of the stented arteries were obtained for histomorphometric measurements to assess the extent of overstretch injury, the amount of neointimal hyperplasia, and restenosis. The coronary vessels from one vehicle-treated pig that expired nine days prior to its scheduled QCA and IVUS procedures was analyzed by histological methods only. One ETC-216-treated pig was euthanized six days after the scheduled twenty-eight days procedures due to an error in facility scheduling. In order to presume a fair comparison, the data collected from these two pigs was excluded from the analysis.

In addition, two animals were treated with about a 3-fold concentrated preparation of ETC-216 delivered through the INFILTRATOR. The preparation was found to be too viscous to effectively deliver test agent through the device and was found to cause damage to the device balloon and therefore an increased amount of injury to the arteries limiting the use of device with viscous solutions.

Blood was obtained from all animals over the course of the study for the determination of white blood cell count, red blood cell count, blood hemoglobin content, percent hematocrit, blood platelet counts. In all cases where these blood variables were determined, post-treatment values did not vary appreciably from the baseline values. That is, they were all within the normal range. Heart rate and blood pressure were determined for all animals entered in the study at baseline. Heart rate and blood pressure were also periodically determined on most animals during the surgical procedures, and prior to sacrifice. For animals entered into the study these variables did not vary appreciably from baseline values due to either the surgical procedure or treatments.

Quantitative Coronary Angiography (QCA) was determined at three time points, prior to coronary injury, immediately following coronary injuries and stent deployment, and prior to sacrifice. Diameter measurements (mm) were made at an unstented segment proximal to the stent (R1), at the proximal section of the stent (Prox), an average area throughout the length of the stent (Aver), at the distal section of the stent (Dist), and at an unstented segment distal to the stent (R2). Intravascular ultrasound (IVUS) was used to determine stent and lumen area at the distal, middle and proximal region of each stented coronary vessel prior to sacrifice. The difference between these measurements is the neointimal area.

Histomorphometric analysis of stented arteries were used to determine the average cross sectional areas of the adventitial boundary layer (ABL), the external elastic lamina (EEL), the internal elastic lamina (IEL), the lumen (L), the adventitia (A), the media (M), the intima (I), the intima to media ratio (I/M) and an injury score. The injury score is the average of 36 determinations of injury consisting of twelve determinations in each of the proximal (a), middle (b) and distal (c) segments at the strut sites of the stented vessel. Injuries were scored either 0, 1, 2 or 3 with 0 indicating an intact IEL (i.e. no injury) and 3 indicating a ruptured EEL with exposure to the adventitia (i.e. most severe injury).

Intramural, INFILTRATOR delivered ETC-216 treatment significantly reduced the intimal to media ratio in coronary vessels by 35 percent (LAD, LCX, and RCA combined). This effect was largely due to significant reductions of the I/M ratio of the RCA (−42%, p=0.002), LCX (−38%), and LAD (−29%). The histomorphometric data for all vessels (i.e. the RCA, LCX and LAD combined) and for vessel type (i.e. the RCA or the LAD) are shown graphically in FIGS. 5a and 5b, respectively.

We claim:

1. A method for reducing restenosis on diseased coronary, peripheral or cerebral arteries in a subject, comprising:
   providing a composition consisting essentially of apolipoprotein A-I Milano (SEQ ID NO:2), a lipid and a pharmaceutically acceptable carrier; and
   administering the composition locally at the site of injury prior to angioplasty during a procedure wherein angioplasty is also performed, or during angioplasty, on the subject to reduce restenosis,
   wherein the restenosis is caused by injury to the coronary, peripheral or cerebral arteries during angioplasty or stent implantation.

2. The method of claim 1, wherein the ratio of apolipoprotein A-I Milano (SEQ ID NO:2) to the lipid by weight is between approximately 1:0.5 and 1:3.

3. The method of claim 1, wherein the lipid is palmitoyl-oleoyl-phosphatidylcholine (POPC).

4. The method of claim 1, wherein the composition is administered by an intramural infiltration device.

5. The method of claim 1, wherein the composition is administered with a catheter.

6. The method of claim 1, wherein the apolipoprotein A-I Milano (SEQ ID NO:2) is in a dose range between 0.01 mg of apolipoprotein/kg and 0.4 mg of apolipoprotein/kg.

7. The method of claim 6, wherein the apolipoprotein A-I Milano (SEQ ID NO:2) is in a dose of 0.3 mg of apolipoprotein/kg.

8. The method of claim 1, wherein the composition is administered in a single effective dosage.

9. The method of claim 1, wherein the composition is administered in multiple dosages.

10. The method of claim 1, wherein the local delivery is achieved through release from a catheter into the subject's pericardial space.

11. The method of claim 1, wherein the local delivery is achieved through release from a coated stent.

12. A method for reducing restenosis on diseased coronary, peripheral or cerebral arteries in a subject, comprising:
    providing a composition consisting essentially of apolipoprotein A-I Milano (SEQ ID NO:2), palmitoyl-oleoyl-phosphatidylcholine (POPC) and a pharmaceutically acceptable carrier; and
    administering the composition locally at the site of injury with an intramural infiltration device prior to angioplasty during a procedure wherein angioplasty is also performed, or during angioplasty, on the subject to reduce restenosis,
    wherein the restenosis is caused by injury to the coronary, peripheral or cerebral arteries during angioplasty or stent implantation.

13. A method for reducing restenosis on diseased coronary, peripheral or cerebral arteries in a subject, comprising:
    providing a composition consisting essentially of apolipoprotein A-I Milano (SEQ ID NO:2) and a pharmaceutically acceptable carrier; and
    administering the composition locally at the site of injury prior to angioplasty during a procedure wherein angioplasty is also performed, or during angioplasty, on the subject to reduce restenosis,
    wherein the restenosis is caused by injury to the coronary, peripheral or cerebral arteries during angioplasty or stent implantation.

14. The method of claim 13, wherein the composition is administered by an intramural infiltration device.

15. The method of claim 13, wherein the composition is administered with a catheter.

16. The method of claim 13, wherein the apolipoprotein A-I Milano (SEQ ID NO:2) is in a dose range between 0.01 mg of apolipoprotein/kg and 0.4 mg of apolipoprotein/kg.

17. The method of claim 16, wherein the apolipoprotein A-I Milano (SEQ ID NO:2) is in a dose of 0.3 mg of apolipoprotein/kg.

18. The method of claim 13, wherein the local delivery is achieved through release from a catheter into the subject's pericardial space.

19. The method of claim 13, wherein the local delivery is achieved through release from a coated stent.

20. A method for reducing restenosis on diseased coronary, peripheral or cerebral arteries in a subject, comprising:
    providing a composition consisting essentially of apolipoprotein A-I Milano (SEQ ID NO:2) and a lipid; and
    administering the composition locally at the site of injury prior to angioplasty during a procedure wherein angioplasty is also performed, or during angioplasty, on the subject to reduce restenosis,
    wherein the restenosis is caused by injury to the coronary, peripheral or cerebral arteries during angioplasty or stent implantation.

21. The method of claim 20, wherein the ratio of apolipoprotein A-I Milano (SEQ ID NO:2) to the lipid by weight is between approximately 1:0.5 and 1:3.

22. The method of claim 20, wherein the lipid is palmitoyl-oleoyl-phosphatidylcholine (POPC).

23. The method of claim 20, wherein the composition is administered by an intramural infiltration device.

24. The method of claim 20, wherein the composition is administered with a catheter.

25. The method of claim 20, wherein the apolipoprotein A-I Milano (SEQ ID NO:2) is in a dose range between 0.01 mg of apolipoprotein/kg and 0.4 mg of apolipoprotein/kg.

26. The method of claim 25, wherein the apolipoprotein A-I Milano (SEQ ID NO:2) is in a dose of 0.3 mg of apolipoprotein/kg.

27. The method of claim 20, wherein the local delivery is achieved through release from a catheter into the subject's pericardial space.

28. The method of claim 20, wherein the local delivery is achieved through release from a coated stent.

29. A method for reducing restenosis on diseased coronary, peripheral or cerebral arteries in a subject, comprising:
   providing a composition consisting essentially of apolipoprotein A-I Milano (SEQ ID NO:2); and
   administering the composition locally at the site of injury prior to angioplasty during a procedure wherein angioplasty is also performed, or during angioplasty, on the subject to reduce restenosis,
   wherein the restenosis is caused by injury to the coronary, peripheral or cerebral arteries during angioplasty or stent implantation.

30. The method of claim 29, wherein the composition is administered by an intramural infiltration device.

31. The method claim 29, wherein the composition is administered with a catheter.

32. The method of claim 29, wherein the apolipoprotein A-I Milano (SEQ ID NO:2) is in a dose range between 0.01 mg of apolipoprotein/kg and 0.4 mg of apolipoprotein/kg.

33. The method of claim 32, wherein the apolipoprotein A-I Milano (SEQ ID NO:2) is in a dose of 0.3 mg of apolipoprotein/kg.

34. The method of claim 29, wherein the local delivery is achieved through release from a catheter into the subject's pericardial space.

35. The method of claim 29, wherein the local delivery is achieved through release from a coated stent.

* * * * *